United States Patent [19]
Cook et al.

[11] Patent Number: 5,861,493
[45] Date of Patent: Jan. 19, 1999

[54] PROCESS FOR THE SYNTHESIS OF 2'-O-SUBSTITUTED PYRIMIDINES

[75] Inventors: Phillip Dan Cook, San Marcos; Robert H. Springer, Carlsbad; Kelly G. Sprankle, Vista; Bruce S. Ross, Carlsbad, all of Calif.

[73] Assignee: Isis Pharmaceuticals, Inc., Carlsbad, Calif.

[21] Appl. No.: 890,084

[22] Filed: Jul. 9, 1997

Related U.S. Application Data

[63] Continuation of Ser. No. 475,467, Jun. 7, 1995, Pat. No. 5,760,202, which is a continuation-in-part of Ser. No. 398,901, Mar. 6, 1995.

[51] Int. Cl.$^6$ .......................... C07H 19/00; C07H 21/00; C07H 21/02
[52] U.S. Cl. ...................... 536/22.1; 536/23.1; 536/25.3
[58] Field of Search ............................... 536/221.1, 23.1, 536/25.3

[56] References Cited

U.S. PATENT DOCUMENTS

| | | | |
|---|---|---|---|
| 3,687,808 | 8/1972 | Merigan et al. | 195/28 N |
| 5,210,264 | 5/1993 | Yau | 558/167 |
| 5,386,023 | 1/1995 | Sanghvi et al. | 536/25.3 |
| 5,470,967 | 11/1995 | Huie et al. | 536/24.3 |

FOREIGN PATENT DOCUMENTS

| | | |
|---|---|---|
| 1-85456 | 4/1989 | Japan . |
| 2-264792 | 10/1990 | Japan . |
| WO 93/10820 | 10/1993 | WIPO . |
| WO 94/02499 | 3/1994 | WIPO . |
| WO 94117094 | 4/1994 | WIPO . |
| WO 95/35102 | 12/1995 | WIPO . |

OTHER PUBLICATIONS

Coddington, J.F. et al., "Nucleosides, XVIII. Synthesis of 2'–Fluorothymidine, 2'–Fluorodeoxyuridine, and Other 2'–Halogeno–2'Deoxy Nucleosides", *J. Org. Chem.*, 1964, 29, pp. 558–564.

Brown, D.M., et al., "Deoxynucleosides and Related Compounds. Part VI, The Synthesis of 2–Thiouridine and of 3'–Dioxyuridine", *J. Chem. Soc.*, 1958, pp. 3028–3035.

McGee, D.P.C. et al., "Novel Nucleosides via Intramolecular Functionalization of 2,2' Anahydrouridine Derivatives", *Tetr. Lett.*, 1996, 37:12, pp. 1995–1998.

Doerr, I.L. and Fox, J.J., "Nucleosides. XXXIX. 2'–Deoxy 2'–flurocytidine, 1 β–D Arabinofuranosyl–2–amino 1, 4(2H)–4–iminopyrimidine and Related Derivatives", *J. Chem. Soc.*, 1967, pp. 1462–1471.

McGee, D.P.C. & Zhai, Y. "Reaction of Anhydronucleosides with Magnesium Alkoxides: Regiospecific Synthesis of 2'–O–Alkylpyrimidine Nucleosides", *Nucleosides and Nucleotides*, 1996, 15(11 and 12), pp. 1797–1803).

McGee, D.P.C. & Zhai, Y., "Reaction of Anhydronucleosides with Magnesium Alkoxides: Regiospecific Synthesis of 2'–O–alkylpyrimidines", *Book of Abstracts–Americian Chem.Soc.*, 1996.

Nucleoside Analogues:Chemistry, Biology, and Medical Applications, Walker, R.T., DeClercq, E. and Eckstein, F., Eds., Plenum Press, 1979, pp. 92–164.

McGee, D.P.C., et al., "Efficient Synthesis of 2'–Amino–2–Deoxypyrimidine 5'–Triphosphates", *Nucleosides and Nucleotides*, 1995, 14(6), pp. 1329–1339.

Townsend, L.B., Chemistry of Nucleosides and Nucleotides, vol. 1, Plenum Press, NY, 1988, pp. 59–67 and 95–112.

Lamond, et al., "Antisense Oligonucleotides Made of 2'–O–alkyRNA: Their Properties and Applications in RNA Biochemistry," *Fed. Of European Biochemical Societies*, 1993, 325 (1–2), pp. 123–127.

Wagner, R., "Antisense Gene Inhibition by Oligonucleotides Containing C–5 Propyne Pyrimidines", *Science*, 1993, 260, pp. 1510–1513.

Alul, R. et al., "Oxalyl–CPG: a Labile Support for Synthesis of Sensitive Oligonucleotide Derivatives", *Nucleic Acids Research* 1991, 19(7), 1527–1532.

Beaucage, S. and Iyer, "Advances in the Synthesis of Oligonucleotides by the Phosphoramidite Approach", *Tetrahedron* 1992, 48(12), 2223–2311.

Bielinska, A. et al., "Regulation of Gene Expression with Double–Stranded Phosphorothioate Oligonucleotides", *Science* 1990, 250, 997–1000.

Blackburn, G. and Gait, "Nucleic Acids in Chemistry and Biology", Chapter 3, p. 98, IRL PRess, New York, 1990.

Bradford, M., "A Rapid and Sensitive Method for the Quantitation of Microgram Quantities of Protein Utilizing the Principle of Protein–Dye Binding", *Analytical Biochemistry* 1976, 72, 248–254.

Coussens, L. et al., "Multiple, Distinct Forms of Bovine and Human Protein Kinase C Suggest Diversity in Cellular Signaling Pathways", *Science* 1986, 233, 859–866.

Dean, N. et al., "Inhibition of Protein Kinase C–α Expression in Human A549 Cells by Antisense Oligonucleotides Inhibits Induction of Intercellular Adhesion Molcelule 1 (ICAM–1) mRNA by Phorbol Esters", *The J. of Biol. Chem.* 1994, 269(23), 16416–16424.

Englisch, U. and Gauss, "Chemically Modified Oligonucleotides as Probes and Inhibitors", *Agnew. Chem. Int. Ed. Engl.* 1991, 30, 613–629.

Gibson, K. and Benkovic, "Synthesis and Application of Derivatizable Oligonucleotides", *Nucleic Acids Research* 1987, 15(16), 6455–6467.

Graham, F.G. and Van der Eb, "A New Technique for the Assay of Infectivity of Human Adenovirus 5 DNA", *Virology* 1973, 52, 456–467.

(List continued on next page.)

Primary Examiner—Ardin H. Marschel
Assistant Examiner—Jezia Riley
Attorney, Agent, or Firm—Woodcock Washburn Kurtz Mackiewicz & Norris LLP

[57] ABSTRACT

Improved processes for the synthesis of 2'-O-substituted pyrimidine nucleosides are provided. The processes feature alkylation of a 2,2'-anhydropyrimidine nucleoside or a 2S,2'-anhydropyrimidine nucleoside with a weak nucleophile in the presence of a Lewis acid.

12 Claims, No Drawings

OTHER PUBLICATIONS

Greene, T. and Wuts, "Protective Groups in Organic Synthesis", John Wiley & Sons, New York, 2nd edition, 1991, Chap. 2, 6, 7.

Haralambidis, J. et al., "Preparation of Base–Modified Nucleosides Suitable for Non–Radioactive Label Attachment and Their Incorporation Into Synthetic Oligodeoxyribonucleotides", *Nucleic Acids Research* 1987, 15(12), 4857–4875.

Kroschwitz, J., ed., "Concise Encyclopedia of Polymer Science and Engineering", pp. 858–859, John Wiley & Sons, New York, 1990.

Manoharan, M., "Designer Antisense Oligonucleotides: Conjugation Chemistry and Functionality Placement", pp. 310–312 in Antisense Research and Applications, Crooke and Lebleu, eds., CRC Press, Boca Raton, 1993.

Miesfeld, R. et al., "Genetic Complementation of a Glucocoricoid Receptor Deficiency by Expression of Cloned Receptor cDNA", *Cell* 1986, 46, 389–399.

Vorbruggen, H. et al., "A Simple New Synthesis of 2–Thiopyrimidine Nucleosides", *Angew. Chem. Internat. Edit.* 1969, 12, 976–977.

Vorbruggen, H. and Strehlke, "Eine einfache Synthese von 2–Thiopyrimidin–nucleosiden", *Chem. Ber.* 1973, 106, 3039–3061.

Wright, P. et al., "Large Scale Synthesis of Oligonucleotides via Phosphoramidite Nucleosides and a High–loaded Polystyrene Support", *Tetrahedron Letters* 1993, 34(21), 3373–3376.

Wu, H. et al., "Inhibition of In Vitro Transcription by Specific Double–Stranded Oligodeoxyribonucleotides", *Gene* 1990, 89, 203–209.

Borer, P.N. et al., "Stability of Ribonucleic Acid Double–Stranded Helices", *J. Mol. Biol.* 1974, 86, 843–853.

Damha, M.J. et al., "An Improved Procedure for Derivatization of Controlled–pore Glass Beads for Solid–phass Oligonucleotide Synthesis", *Nucliec Acids Research* 1990, 18, 3813–3821.

Freier, S.M. et al., in "Gene Regulation; Biology of Antisense RNA and DNA", Fox, C.F., ed., Raven Press, New York, 1992, pp. 95–107.

Freier, S.M. et al., "Solvent Effects of the Dynamics of $(dG-dC)_3$", *Biopolymers* 1983, 22, 1107–1131.

Guinosso, C.J. et al., "Synthesis and Biophysical and Biological Evaluation of 2'–Modified Antisense Oligonucleotides", *Nucleosides and Nucleotides* 1991, 10, 259–262.

Lesnik, E.A. et al., "Oligodeoxynucleotides Containing 2'–O–Modified Adenosine: Synthesis and Effects on Stability of DNA:RNA Duplexes", *Biochemistry* 1993, 32, 7832–7838.

Monia, B.P. et al., "Selective Inhibition of Mutant Haras mRNA Expression by Antisense Oligonucleotides", *J. Biol. Chem.* 1992, 267, 19954–19962.

Monia, B.P. et al., "Evaluation of 2'–Modified Oligonucleotides Containing 2'–Deoxy Gaps as Antisense Inhibitors of Gene Expression", *J. Biol. Chem.* 1993, 268, 14514–14522.

Petersheim, M. and Turner, "Base–Stacking and Base–Pairing Contributions to Helix Stability: Thermodynamics of Double–Helix Formations with CCGG, CCGGp, CCGGAp, ACCGGp, CCGGUp, and ACCGGUp", *Biochemistry* 1983, 22, 256–263.

Puglisi, J. and Tinoco, "Absorbance Melting Curves of RNA", *Methods in Enzymology* 1989, 180, 304–325.

Ueda, T. and Tanaka, "Synthesis of 2–Thiouridine and 6–Methyl–3–(β–D–ribofuranosyl)–2–Thiouracil", *Chem. Pharm. Bull.* (*Tokyo*) 1970, 18, 1491–1493.

Morvan, et al., "Comparative Evaluation of Seven Oligonucleotide Analogues as Potential Antisense Agents, " *Jour.Med. Chem.,* 1993, vol.36, pp. 280–287.

Kawasaki, et al., "Uniformly Modified 2'–Deoxy–2'–Fluoro Phosphorothioate Oligonucleotides as Nuclease–Resistant Antisensse Compounds w/High Affinity & Specificity for RNA Targets", *Jour.Med. Chem.,* 1993, vol. 36, pp. 831–841.

Holy, A., Nucleic Acid Components and Their Analoguesm CLV, *Coll. Czech. Chem. Commun.,* 1973, pp. 423–427.

Sterzycki et al. "Synthesis and Anti–HIV Activity of Several 2'–Fluoro–Containing Pyrimidine Nucleosides" J. Med. Chem., vol. 33, pp. 2150–2157, 1990.

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGACCGGAAG GTACGAG                                  17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGACCGGAAG GUACGAG                                  17

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGACCGGAAG GUACGAG                                  17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGACCGGAAG GUACGAG                                  17

( 2 ) INFORMATION FOR SEQ ID NO:5:

( i ) SEQUENCE CHARACTERISTICS:
        ( A ) LENGTH: 17 base pairs
        ( B ) TYPE: nucleic acid (C) STRANDEDNESS: single
    (D) TOPOLOGY: linear (xi) SEQUENCE DESCRIPTION: SEQ ID NO:5:

GGACCGGAAG GTACGAG                                             17

(2) INFORMATION FOR SEQ ID NO:6:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (xi) SEQUENCE DESCRIPTION: SEQ ID NO:6:

CUAAGCAUGU CA                                                  12

(2) INFORMATION FOR SEQ ID NO:7:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (xi) SEQUENCE DESCRIPTION: SEQ ID NO:7:

CUAAGCAUGU CA                                                  12

(2) INFORMATION FOR SEQ ID NO:8:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (xi) SEQUENCE DESCRIPTION: SEQ ID NO:8:

CUAAGCAUGU CA                                                  12

(2) INFORMATION FOR SEQ ID NO:9:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (xi) SEQUENCE DESCRIPTION: SEQ ID NO:9:

CUAAGCAUGU CA                                                  12

(2) INFORMATION FOR SEQ ID NO:10:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (xi) SEQUENCE DESCRIPTION: SEQ ID NO:10:

CUAAGCAUGU CA                                                  12

(2) INFORMATION FOR SEQ ID NO:11:

(i) SEQUENCE CHARACTERISTICS:
    (A) LENGTH: 12 base pairs
    (B) TYPE: nucleic acid
    (C) STRANDEDNESS: single
    (D) TOPOLOGY: linear ( x i ) SEQUENCE DESCRIPTION: SEQ ID NO:11:

CUAAGCAUGU CA                                                                           12

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CGACTATGCA AGTAC                                                                        15

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CGACTATGCA AGTAC                                                                        15

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CGACTATGCA AGTAC                                                                        15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CGACTATGCA AGTAC                                                                        15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CGACTATGCA AGTAC                                                                        15

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGACCGGAAG GTACGAG 17

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGACCGGAAG GUACGAG 17

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGACCGGAAG GUACGAG 17

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGACCGGAAG GUACGAG 17

( 2 ) INFORMATION FOR SEQ ID NO:21:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GGACCGGAAG GTACGAG 17

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

TGGGAGCCAT AGCGAGGC 18

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

TGGGAGCCAT AGCGAGGC 18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:24:

TGGGAGCCAT AGCGAGGC                                           18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:25:

TGGGAGCCAT AGCGAGGC                                           18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (x i) SEQUENCE DESCRIPTION: SEQ ID NO:26:

TGGGAGCCAT AGCGAGGC                                           18

PROCESS FOR THE SYNTHESIS OF 2'-O-SUBSTITUTED PYRIMIDINES

CROSS REFERENCE TO RELATED APPLICATIONS

This is a continuation of application Ser. No. 08/475,467, filed Jun. 7, 1995, now U.S. Pat. No. 5,760,202 which is a continuation-in-part of application Ser. No. 08/398,901, filed Mar. 6, 1995, the disclosure of which is herein incorporated by reference.

FIELD OF THE INVENTION

This invention is directed to improved processes for the synthesis of 2'-O-substituted pyrimidine nucleosides. The invention features treating a 2,2'-anhydropyrimidine nucleoside or a 2S,2'-anhydropyrimidine nucleoside with a weak nucleophile and a Lewis acid. The process is economically advantageous relative to processes currently in use and is applicable to large scale synthesis.

BACKGROUND OF THE INVENTION

2'-O-Substituted pyrimidine nucleosides are useful per se in the preparation of oligonucleotides and related compounds. 2'-O-Substituted pyrimidine nucleosides are commercially available from companies such as, for example, Glen Research, Sterling, Va., and are considered to be items of commerce. The present invention is directed to new and useful processes for the preparation of 2'-O-substituted pyrimidine nucleosides.

Oligonucleotides and their analogs have been developed for various uses in molecular biology, including use as probes, primers, linkers, adapters, and gene fragments. Modifications to oligonucleotides used in these procedures include labeling with nonisotopic labels such as fluorescein, biotin, digoxigenin, alkaline phosphatase or other reporter molecules. Modifications also have been made to the ribose phosphate backbone to increase the nuclease stability of the resulting analog. These modifications include use of methyl phosphonates, phosphorothioates, phosphorodithioate linkages, and 2'-O-methyl ribose sugar units. Other modifications have been directed to the modulation of oligonucleotide uptake and cellular distribution. The success of these oligonucleotides for both diagnostic and therapeutic uses has created an ongoing demand for improved oligonucleotide analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is a general object of such therapeutic approaches to interfere with or otherwise modulate gene expression which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as antisense agents in human clinical trials for various disease states, including use as antiviral agents.

Transcription factors interact with double-stranded DNA during regulation of transcription. Oligonucleotides can serve as competitive inhibitors of transcription factors to modulate the action of transcription factors. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides have also found use in the diagnostic testing of materials including, for example, biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligonucleotides via Watson-Crick and/or Hoogsteen base pairs to RNA or DNA. The bases of such base pairs are said to be complementary to one another.

Oligonucleotides are also widely used as research reagents. They are particularly useful in studies exploring the function of biological molecules, as well as in the preparation of biological molecules. For example, the use of both natural and synthetic oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR.

Oligonucleotides are also used in other laboratory procedures. Several of these uses are described in common laboratory manuals such as *Molecular Cloning, A Laboratory Manual,* Second Ed., J. Sambrook, et al., Eds., Cold Spring Harbor Laboratory Press, 1989; and *Current Protocols In Molecular Biology,* F. M. Ausubel, et al., Eds., Current Publications, 1993. Representative of such uses are as Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA (see Book 2 of *Molecular Cloning, A Laboratory Manual,* supra) and DNA-Protein Interactions and The Polymerase Chain Reaction (see Vol. 2 of *Current Protocols In Molecular Biology,* supra).

Oligonucleotides can be synthesized to have custom properties that are tailored for a desired use. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Gibson, K. J., and Benkovic, S. J., *Nucleic Acids Research,* 1987, 15, 6455–6467, report a phthalimide-protected 5-(3-aminopropyl)-2'-deoxyuridine nucleoside probe, which is incorporated into oligonucleotides.

Haralambidis, J., et. al., *Nucleic Acids Research*, 1987, 15, 4857–4876, reports C-5 substituted deoxyuridines which are incorporated into oligonucleotides. The substituent has a masked primary aliphatic amino group which can be further substituted with various groups.

PCT Application WO 94/17094, filed Jan. 22, 1993, published Aug. 4, 1994, reports 5-substituted pyrimidine (cytosine or uracil) bases wherein the 5-substituent is $C_{3-14}$ n-alkyl, $C_{2-8}$ (E)-n-1-alkenyl, ethynyl, or a $C_{4-12}$ n-1-alkyl group, and the synthesis of oligonucleotides having one or more of the modified 5-substituted pyrimidine bases.

PCT Application No. WO 93/10820, filed Nov. 24, 1992, published Jun. 10, 1993, reports 5-(1-propynyl)uracil and 5-(1-propynyl)cytosine or related analogs, and the synthesis of oligonucleotides having one or more of the modified 5-substituted pyrimidine bases.

PCT Application No. WO 93/10820, filed Nov. 24, 1992, reports 2'- and 5-substituted pyrimidine nucleotides which are incorporated into oligonucleotides having a pi bond connecting the carbon atom attached to the 5' position of the base.

SUMMARY OF THE INVENTION

In accordance with this invention there are provided improved processes for the synthesis of 2'-O-substituted pyrimidine nucleosides of formula:

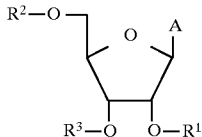

wherein:

Q is a pyrimidine base or a 2-S pyrimidine base;

$R^1$ is substituted or unsubstituted $C_1$–$C_{30}$ alkyl, $C_1$–$C_{30}$ alkenyl, $C_1$–$C_{30}$ alkynyl, $C_6$–$C_{14}$ aryl, or $C_7$–$C_{30}$ aralkyl, wherein said substitution is halo, amino, hydroxyl, thiol, ether or thioether; and $R^2$ and $R^3$ are independently hydrogen or a hydroxyl protecting group;

comprising the steps of:

providing a 2-2'-anhydropyrimidine nucleoside;

selecting an alcohol of the formula $R^1$-OH; and treating said 2-2'-anhydropyrimidine nucleoside and said alcohol with a Lewis acid under conditions of time, temperature and pressure effective to yield said 2'-O-substituted pyrimidine nucleoside.

In accordance with this invention there are also provided improved processes for the synthesis of a 2'-O-substituted cytidine nucleoside of formula:

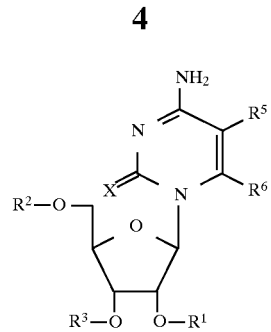

wherein:

X is O or S;

$R^1$ is substituted or unsubstituted $C_1$–$C_{30}$ alkyl, $C_1$–$C_{30}$ alkenyl, $C_1$–$C_{30}$ alkynyl, $C_6$–$C_{14}$ aryl, or $C_7$–$C_{30}$ aralkyl, wherein said substitution is halo, amino, hydroxyl, thiol, ether or thioether;

$R^2$ and $R^3$ are independently hydrogen or a hydroxyl protecting group;

$R^5$ and $R^6$ are independently H, $C_1$–$C_{30}$ hydrocarbyl or substituted $C_1$–$C_{30}$ hydrocarbyl;

comprising the steps of:

providing a 2-2'-anhydrouridine nucleoside of formula:

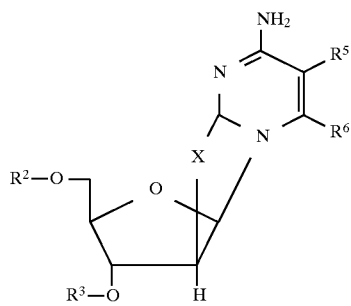

selecting an alcohol of formula $R^1$-OH;

treating said 2-2'-anhydrouridine nucleoside and said alcohol with a Lewis acid under conditions of time, temperature and pressure effective to form a 2'-O-substituted uridine nucleoside; and aminating said 2'-O-substituted uridine nucleoside to said 2'-O-substituted cytidine nucleoside.

In preferred embodiments of the invention the 2-2'-anhydropyrimidine nucleoside and the alcohol of the formula $R^1$-OH are treated in a pressure sealed vessel as the reaction vessel, for example a pressure bomb. Preferably, the reaction vessel is heated from about 120° C. to about 200° C.

In a further embodiment of the invention the Lewis acid is a borate, particularly a trialkyl borate. Preferably, the alkyl groups of the trialkyl borate are the same as the R group of the alcohol, so the formula of the borate is $B(OR^1)_3$. The trialkyl borate is preferably prepared from the treatment of borane with an alcohol. Preferably, the alcohol that is used for the treatment of the 2,2'-anhydropyrimidine nucleoside is also used to prepare the trialkyl borate, preferably an alcohol of formula HO-$R^1$.

In some preferred embodiments of the invention $R^1$ is $C_1$–$C_{30}$ alkyl, more preferably $C_1$–$C_{10}$ alkyl. In another preferred embodiment the $R^1$ is $C_6$–$C_{14}$ aryl.

In one preferred embodiment of the invention the pyrimidine nucleoside prepared by the process is uridine or 5-methyluridine.

In another preferred embodiment of the invention the 2'-O-substituted cytidine nucleoside prepared by the process is uridine or 2'-O-methyl-5-methylcytidine.

DESCRIPTION OF PREFERRED EMBODIMENTS

The processes of the present invention are useful for the synthesis of 2'-O-substituted pyrimidine nucleosides. 2'-O-substituted pyrimidine nucleosides are important compounds used routinely for the synthesis of oligonucleotides and related compounds. Representative commercially available 2'-O-substituted pyrimidine nucleosides include 2'-O-methyl uridine and 2'-O-methyl cytidine.

For the purposes of the present invention, pyrimidine nucleosides include naturally occurring pyrimidines bases such as uridine and cytidine as well as non-naturally occurring pyrimidines such as 2S analogs and 5- and 6-substituted uridines and cytidines. Also included are N3 substituted pyrimidines and pyrimidines having heterocyclic ring structures attached, for example, at position 4 and/or 5. Many modified pyrimidines amenable to the present invention are known in the art (See for example *Chemistry of Nucleosides and Nucleotides, Volume* 1 Plenum Press, N.Y. 1988). As defined herein, a 2S pyrimidine base is a pyrimidine base having a sulfur atom bound to the 2-position thereof.

As defined herein, 2S,2'-anhydropyrimidine nucleosides are pyrimidine nucleosides which have a single bond connecting the 2-position of the pyrimidine ring to the 2'-oxygen of the nucleosidic sugar. 2S,2'-anhydropyrimidine nucleosides, as defined herein, are pyrimidine nucleosides wherein the 2-position of the pyrimidine ring is bound to the 2'-position of the nucleosidic sugar thorough an intervening sulfur atom.

In some preferred embodiments 2S,2'-anhydropyrimidine nucleosides or 2S,2'-anhydropyrimidine nucleosides have the general formula:

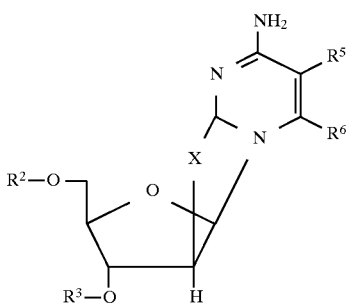

wherein:
X is O or S;
$R^2$ and $R^3$ are independently hydrogen or a hydroxyl protecting group; and
$R^5$ and $R^6$ are independently H, $C_1$–$C_{30}$ hydrocarbyl or substituted $C_1$–$C_{30}$ hydrocarbyl;

2S,2'-Anhydropyrimidine nucleosides and 2S,2'-anhydropyrimidine nucleosides suitable for use in the processes of the invention include those that are unsubstituted as well as those having substitutions on the pyrimidine ring. A variety of such substituted pyrimidine substitutions are known in the art, for example, alkylation at the 5-position. See for example *Chemistry of Nucleosides and Nucleotides,* Volume 1 supra. Such substituted 2,2' and 2S,2'-anhydropyrimidine nucleosides can be prepared from a naturally occurring nucloeside which can be modified before or after formation of the 2,2' or 2S,2' bond. Thus, in one aspect of the present invention, substituents are attached to the 2,2' or 2S,2'-anhydropyrimidine nucleoside after formation of the 2,2' or 2S,2' bond, and in another aspect of the invention the attachment of substituents to the pyrimidine ring of the pyrimidine nucleoside precedes formation of the 2,2' or 2S,2'-anhydropyrimidine nucleoside.

The process of the present invention provides significant economic benefits in the production of 2'-O-substituted pyrimidines. For example, the compound 2'-O-methyl uridine, which is an important intermediate in the synthesis of modified oligonucleotides and related compounds, can be prepared at about one tenth the cost of the commercially available material using the process of the present invention. Another useful intermediate, 2'-O-methyl-cytidine, also useful in the synthesis of modified oligonucleotides and related compounds, can be prepared at about one fifth the cost of the commercially available material using the process of the present invention. These costs are based on yields previously obtained for large scale synthesis, the price of the starting materials, and the hours of labor required.

2,2'-Anhydropyrimidine nucleosides can be prepared from pyrimidine nucleosides by treatment with diphenylcarbonate and sodium bicarbonate in DMF, or other traditional solvents, followed by purification. See e.g., Townsend, Leroy B., *Chemistry of Nucleosides and Nucleotides* 1, Plenum Press, New York, 1988). The resulting 2,2'-anhydropyrimidine nucleosides are treated with a weak nucleophile (e.g. an alcohol) and a Lewis acid (e.g. a trialkyl borate) with heating to give the corresponding 2'-O-substituted pyrimidine nucleoside. In preferred embodiments of the present invention, a 2S,2', or 2,2'-anhydropyrimidine nucleoside is treated with an alcohol of formual $R^1$-OH in the presence of a weak nucleophile to give the respective 2'-O-$R^1$-pyrimidine nucleoside or 2S analog. The process is amenable to both small and large scale synthesis of 2'-O-substituted pyrimidine nucleosides.

2S,2'-Anhydropyrimidine nucleosides can be made from pyrimidine nucleosides following the procedure of, for example, Townsend, Leroy B., supra. See also Ueda, T., Tanaka, H., *Chem. Pharm. Bull.* (Toykyo), 1970, 18, 149. The 2S,2'-anhydropyrimidine nucleoside can then be treated with a weak nucleophile (e.g. an alcohol) and a Lewis acid (e.g. a trialkyl borate) according to the methods of the invention to give the corresponding 2'-O-substituted 2S-pyrimidine nucleoside.

2'-O-substituted pyrimidine nucleosides and 2'-O-substituted 2S-pyrimidine nucleosides can be converted into their respective DMT/amidites following standard methods and techniques to give the 1-[5-O-dimethoxytrityl-2-O-substituted-(3-O-N,N-diisopropylamino-2-cyanoethylphosphite)]pyrimidine nucleoside or the 1-[5-O-dimethoxytrityl-2-O-substituted-(3-O-N,N-diisopropylamino-2-cyanoethylphosphite)]-2S-pyrimidine nucleoside, each of which can be used as a monomeric subunit precursor in the synthesis of oligomeric compounds.

While we do not wish to be bound by a specific theory, it is thought that the mechanism of opening of the anhydropyrimidine nucleoside ring involves nucleophilic attack at the 2'-carbon by a weak nucleophile. It is thought that the nucleophilic attack is facilitated by the complexing of the Lewis acid to the bridging oxygen. The resulting complex is believed to activate the 2'-carbon to nucleophilic attack by the weak nucleophile. Another theory that may be applicable is that the Lewis acid complexes to the 5' and 3' hydroxyl groups, causing a conformational change in the molecule, enabling attack by the weak nucleophile to give the product.

In one embodiment of the invention the Lewis acid used is a trialkyl borate. The trialkyl borate can be purchased or prepared such that the borate alkyl groups are identical to the alkyl groups of the nucleophile. For example, when 2'-O-methyluridine is being prepared, trimethyl borate would preferably be the Lewis acid, and methanol preferably would be the nucleophile. Trimethyl, triethyl, and tripropyl borates are commercially available through Aldrich Chemical Company, Milwaukee, Wis.

Alternatively, trialkyl borates can be prepared from borane and the alcohol that corresponds to the desired substituent for the 2'-position as illustrated above. Typically, borane, which is available as a 1.0M solution in THF, is reacted with 3 equivalents of the respective alcohol. When the evolution of hydrogen is completed the solution is concentrated to remove the THF. The resulting solution, which contains the desired trialkyl borane in the desired alcohol, can be used in the instant process to achieve opening of the anhydro ring as discussed above.

In one aspect of the present invention 2'-O-substituted pyrimidine nucleosides wherein the pyrimidine is a uridine or a substituted uridine can be converted (aminated) to the corresponding cytidine analog by known methods and techniques using, for example, 1,2,4-triazole. Typically, a 2'-O-substituted uridine nucleoside is first protected at the 3'-O and 5'-O positions with a traditional protecting group such as, for example, acetic anhydride. 1,2,4-Triazole, in a traditional solvent (e.g. acetonitrile), is treated with $POCl_3$ in the presence of a base (e.g. triethylamine) at low temperature. The protected 2'-O-substituted uridine nucleoside is dissolved in a traditional solvent and added to the solution containing triazole/$POCl_3$. After sufficient time has passed, subsequent workup and purification yield the triazine-1-(3, 5-di-O-protected-2-substituted)pyrimidine nucleoside. This compound can be converted into the cytosine analog by treatment with ammonia. The exocycloamino group can be protected, for example by treatment with benzoic anhydride, in a traditional solvent such as, for example, pyridine.

In a further aspect of the present invention 2'-O-substituted-2S-pyrimidine nucleosides wherein the pyrimidine is a uridine or a substituted uridine can be converted to the corresponding cytidine analog by known methods and techniques using 1,2,4-triazole. The procedure presented above is followed except that the 2S group is protected with an appropriate protecting group, e.g. toluoyl, prior to treatment with triazole.

The resulting 2'-O-substituted-uridine or 2'-O-substituted-2S-uridine can be converted into the respective DMT/amidite following standard methods and techniques to give 4-N-protected-1-(2-O-substituted-3-O-N,N-diisopropylamino-2-cyanoethylphosphite-5-O-dimethoxytrityl)cytidine or the 2S analog. The 4-N-protected-1-(2-O-substituted-3-O-N,N-diisopropylamino-2-cyanoethylphosphite-5-O-dimethoxytrityl)cytidine or the 2S analog can be used as a monomeric sub-unit precursor in the synthesis of oligomeric compounds.

Pyrimidines bearing a variety of substitutions (i.e., pyrimidines bearing substituent groups) are known in the art. A representative list of such substituent groups amenable to the process of the present invention includes hydrocarbyl groups such as alkyl or substituted alkyl, alkenyl or substituted alkenyl, alkynyl or substituted alkynyl, carbocylo alkyl, carbocylo alkenyl, carbocylo aralkyl, aryl, aralkyl or substituted aralkyl. Preferably, the alkyl, alkenyl and alkynyl substituent groups have from 1 to about 30 carbons, with 1 to about 10 carbons being particularly preferred. Preferably, the aryl groups have from 6 to about 14 carbons, and aralkyl groups have from 7 to about 30 carbons. The substituent groups listed above can themselves bear substituent groups such as alkoxy, alcohol, benzyl, phenyl, nitro, thiol, thioalkoxy, halogen, or alkyl, aryl, alkenyl, or alkynyl groups, and ether groups.

Substitution of alkyl, alkenyl, and alkynyl groups at C-5 of uracil is reported in PCT application PCT/US92/10115, filed Nov. 24, 1992, and examples of alkyl substitutions are further disclosed by Manoharan, M., *Antisense Research and Applications,* Crooke and Lebleu, eds., CRC Press, Boca Raton, 1993. Further substitutions are reported in Townsend, L. B, ibid.

In the process of the present invention, a 2S,2' or 2,2'-anhydro pyrimidine nucleoside is treated with an alcohol of formula $R^1$-OH. Representative $R^1$ groups include alkyl or substituted alkyl, alkenyl or substituted alkenyl, alkynyl or substituted alkynyl, carbocylo alkyl, carbocylo alkenyl, carbocylo aralkyl, aryl, aralkyl or substituted aralkyl. Preferably, the alkyl, alkenyl and alkynyl R groups have from 1 to about 30 carbons, with 1 to about 10 carbons being particularly preferred. Preferably, aryl groups have from 6 to about 14 carbons, and aralkyl groups have from 7 to about 30 carbons. The $R^1$ groups listed above can themselves bear substituent groups such as alkoxy, alcohol, amino, benzyl, phenyl, nitro, thiol, thioalkoxy, halogen, hydroxy, ether or further alkyl, aryl, alkenyl, or alkynyl groups.

2'-O-substituted pyrimidine nucleosides and 2'-O-substituted 2S-pyrimidine nucleosides (substituted pyrimidine nucleosides) prepared according to the process of the present invention can be used to prepare a variety of compounds including oligonucleotides, oligonucleosides, mixed oligonucleotides/nucleosides, and related compounds known in the art.

In the context of this invention, the term "oligonucleotide" includes oligomers or polymers containing two or more nucleotide subunits. Nucleotides, as used herein, may include naturally occurring sugars, nucleobases, and intersugar (backbone) linkages as well as non-naturally occurring portions which function similarly. Such chemically modified or substituted oligonucleotides are often preferred over native forms because of properties such as, for example, enhanced cellular uptake and increased stability in the presence of nucleases.

Specific examples of some preferred oligonucleotides envisioned for this invention may contain, in addition to phosphodiester intersugar linkages (backbones), modified intersugar linkages such as phosphorothioates, phosphotriesters, methyl phosphonates, chain alkyl or cycloalkyl intersugar linkages or short chain heteroatomic or heterocyclic intersugar linkages.

As used herein, the term oligonucleoside includes oligomers or polymers containing two or more nucleoside subunits having a non-phosphorous linking moiety. Oligonucleosides according to the invention have a ribofuranose moieties attached to a nucleobases through glycosyl bonds.

An oligo-nucleotide/nucleoside for the purposes of the present invention is a mixed backbone oligomer having at least two nucleosides covalently bound by a non-phosphate linkage and at least one phosphorous containing covalent bond with a nucleotide, and wherein at least one of the monomeric nucleotide or nucleoside units is a 2'-O-substituted compound prepared using the process of the present invention. An oligonucleotide/nucleoside can additionally have a plurality of nucleotides and nucleosides coupled through phosphorous containing and/or non-phosphorous containing linkages.

Methods of coupling 2'-O-substituted compounds prepared using the process of the present invention include conversion to the phosphoramidite followed by solution phase or solid phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods. This allows for synthesis of linkages including phosphodiester or phosphorothioate phosphate linkages depending upon oxidation conditions selected. Other phosphate linkages can also be generated. A representative list of suitable linkages includes phosphodiester, phosphotriester, hydrogen phosphonate, alkylphosphonate, alkylphosphonothioate, arylphosphonothioate, phosphorothioate, phosphorodithioate, phosphoramidate, ketone, sulfone, carbonate, thioamidate and other such moieties as are known in the art. Alkylphosphonothioate linkages are disclosed in WO 94/02499.

For the purposes of this specification, alkyl groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups.

Alkenyl groups useful in the invention include, but are not limited to, moieties derived from the above alkyl groups containing one or more carbon-carbon double bonds such as vinyl, allyl and crotyl.

Alkynyl groups useful in the invention include, but are not limited to, moieties derived from the above alkyl groups containing one or more carbon-carbon triple bonds such as propargyl.

The term aryl is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms.

The term aralkyl is intended to denote groups containing both alkyl and aryl portions wherein the point of attachment of such groups is through an alkyl portion thereof. Benzyl groups provide one example of an aralkyl group.

A number of substituent groups can be introduced into compounds of the invention in a protected (blocked) form and subsequently de-protected to form a final, desired compound. Substituent groups include groups covalently attached to the pyrimidine ring and the $R^1$ group of the alcohol $R^1$-OH described above. In general, protecting groups render chemical functionality inert to specific reaction conditions and can be appended to and removed from such functionality in a molecule without substantially damaging the remainder of the molecule. See, e.g., Greene and Wuts, *Protective Groups in Organic Synthesis*, 2d ed, John Wiley & Sons, New York, 1991. For example, amino groups can be protected as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, and trimethoxytrityl groups.

Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene. Many other solid supports are commercially available and amenable to the present invention.

An activated solid support in the context of the present invention is a solid support that has been derivatized with a functional group or treated with a reactive moiety such that the resulting activated solid support is chemically active towards reaction with a monomeric subunit or a nucleoside dimer of the invention.

Standard methods and techniques used to increase the coupling efficiency of oligonucleotide synthesis include activation of 3' and or 5' functional groups. Some commonly activated groups are phosphate and phosphite, which give the corresponding activated phosphate and activated phosphite (see e.g., *Nucleic Acids in Chemistry and Biology;* Blackburn, G. M., Gait M. J., Eds. Chemical Synthesis; IL: New York, 1990, Chapter 3, p. 98). Many others are known and can be used herein.

In some preferred embodiments the processes of the invention are used to prepare 2'-O-substituted-5-halo pyrimidine nucleosides. 2'-O-substituted-5-halo uridine may be prepared from 5-F, -Cl, -Br, and -I uracils, which are available from Aldrich Chemical Company. The 2'-O-substituted 5-halo uridine can be converted into the cytidine analog as discussed below.

In the process of the invention, the alcohol, lewis acid and anhydropyrimidine nucleoside are treated in a reaction vessel. The reaction vessel may be any container known in the art to be suitable for reactions wherein reactants are heated. Preferably, the reaction vessel is a pressure sealed vessel, and more preferably, a pressure bomb.

In preferred embodiments the alcohol, lewis acid and anhydropyrimidine nucleoside in an appropriate solvent such as dioxane and are treated by heating at from about 120° C. to about 200° C. In especially preferred embodiments the alcohol, lewis acid, anhydropyrimidine nucleoside and solvent are heated in a pressure sealed vessel. A pressure bomb is particularly preferred.

The term Lewis acid, as used herein, has its usual meaning as a molecule or ion which can combine with another molecule or ion by forming a covalent bond with two electrons from the second molecule or ion. Especially preferred examples of Lewis acids useful in the instant process are borates, particularly alkyl borates.

Oligonucleotides including 2'-O-methyl pyrimidine nucleotides have been evaluated in studies to assess their effectiveness in the inhibition of gene expression, as well as their hybridization affinity to complementary RNA. One such study (see Monia, B. P., et.al., *J. Biol. Chem.*, 1993, 268, 14514–14522) using 2'-modified oligonucleotides containing 2'-deoxy gaps and uniformly modified 2'-modified oligonucleotides has shown that the 2'-modified oligonucleotides have greater affinity for complementary RNA than the corresponding unmodified 2'-deoxyoligonucleotides. The 2'-modified oligonucleotides containing 2'-deoxy gaps also showed activity against the expression of the Ha-ras oncogene in cells.

In another study which included uniformly modified 2'-O-substituted oligoribonucleotides, nuclease stabilities and melting temperatures ($T_m$) were compared for fully modified oligoribonucleotide sequences containing 2'-fluoro, 2'-O-methyl, 2'-O-propyl, and 2'-O-pentyl nucleotides. Modifications, with the exception of 2'-O-pentyl, were observed to increase the $T_m$ of duplexes formed with complementary RNA. Modified homoduplexes showed significantly higher $T_m$s, with the following $T_m$ order: 2'-fluoro:2'fluoro>2'-O-propyl:2'-O-propyl>2'-O-methyl:2'-O-methyl>RNA:RNA>DNA:DNA. The nuclease stability of 2'-modified oligoribonucleotides was examined using snake venom phosphodiesterase (SVPD) and nuclease S1. The stability imparted by 2'-modifications was observed to correlate with the size of the modification. An additional level of nuclease stability was present in oligoribonucleotides having the potential for forming secondary structure, but only for 2' modified oligoribonucleotides and not for 2'-deoxy oligoribonucleotides.

Additional objects, advantages, and novel features of this invention will become apparent to those skilled in the art upon examination of the examples thereof provided below.

EXAMPLE 1

2,2'-anhydro[1-(β-D-arabinofuranosyl)-5-methyluridine]

5-Methyluridine (ribosylthymine, commercially available through Yamasa, Choshi, Japan) (72.0 g, 0.279 mol), diphenylcarbonate (90.0 g, 0.420 mol) and sodium bicarbonate (2.0 g, 0.024 mol) were added to dimethylformamide (300 mL). The mixture was heated to reflux with stirring allowing the resulting carbon dioxide gas to evolve in a controlled manner. After 1 hour, the slightly darkened solution was concentrated under reduced pressure. The resulting syrup was poured into stirred diethyl ether (2.5 L). The product formed a gum. The ether was decanted and the residue was dissolved in a minimum amount of methanol (ca 400 Ml). The solution was poured into fresh ether as above (2.5 L) to give a stiff gum. The ether was decanted and the gum was dried in a vacuum oven (60° C. at 1 mm Hg for 24 h) to give a solid which was crushed to a light tan powder (57 g, 85% crude yield). NMR was consistent with structure and contamination with phenol and its sodium salt (ca 5%). The material was used as is for ring opening. It can be purified further by column chromatography using a gradient of methanol in ethyl acetate (10–25%) to give a white solid, mp 222°–4° C.

EXAMPLE 2

1-(2-fluoro-β-D-erythro-pentofuranosyl)-5-methyluridine 2,2'-Anhydro[1-(β-D-arabinofuranosyl)-5-methyluridine] (71 g, 0.32 mmol) and dioxane (700 mL) are placed in a 2 liter stainless steel bomb and HF/pyridine (100 g, 70%) was added. The mixture was heated for 16 hours at 120°–125° C. and then cooled in an ice bath. The bomb was opened and the mixture was poured onto 3 liters of ice. To this mixture was added cautiously sodium hydrogen carbonate (300 g) and saturated sodium bicarbonate solution (400 mL). The mixture was filtered and the filter cake was washed with water (2×100 mL) and methanol (2×500 mL). The water and methanol washes were concentrated to dryness in vacuo. Methanol (200 mL) and coarse silica gel (80 g) were added to the residue and the mixture was concentrated to dryness in vacuo. The resulting material was concentrated onto the silica gel and purified by silica gel column chromatography using a gradient of ethyl acetate and methanol (100:0 to 85:15). Pooling and concentration of the product fractions gave 36.9 g (51%, 2 step yield) of the title compound.

Also isolated from this reaction was 1-(2-phenyl-β-D-erythro-pentofuranosyl)-5-methyluridine (10.3 g). This material is formed from the phenol and its sodium salt from the anhydro reaction above when the bomb reaction is carried out on impure material. When The anhydro material is purified this product is not formed. The formed 1-(2-phenyl-β-D-erythro-pentofuranosyl)-5-methyluridine was converted into its DMT/phosphoramidite using the same reaction conditions as for the 2'-Fluoro material.

EXAMPLE 3

1-(5-O-Dimethoxytrityl-2-fluoro-β-D-erythro-pentofuranosyl) -5-methyluridine 1-(2-fluoro-β-D-erythro-pentofuranosyl)-5-methyluridine (31.15 g, 0.12 mol) was suspended in pyridine (150 mL) and dimethoxytrityl chloride (44.62 g, 0.12 mol) was added. The mixture was stirred in a closed flask for 2 hours and then methanol (30 mL) was added. The mixture was concentrated in vacuo and the resulting residue was partitioned between saturated bicarbonate solution (500 mL) and ethyl acetate (3×500 ml). The ethyl acetate fractions were pooled and dried over magnesium sulfate, filtered and concentrated in vacuo to a thick oil. The oil was dissolved in dichloromethane (100 mL), applied to a silica gel column and eluted with ethyl acetate:hexane:triethylamine, 60/39/1 increasing to 75/24/1. The product fractions were pooled and concentrated in vacuo to give 59.9 g (89%) of the title compound as a foam.

EXAMPLE 4

1-(5-O-Dimethoxytrityl-2-fluoro-3-O-N,N-diisopropylamino-2-cyanoethylphosphite-β-D-erythro-pentofuranosyl)-5-methyluridine 1-(5-O-Dimethoxytrityl-2-fluoro-β-D-erythro-pentofuranosyl)-5-methyluridine (59.8 g, 0.106 mol) was dissolved in dichloromethane and 2-cyanoethyl N,N,N',N'-tetraisopropylphosphorodiamidite (46.9 mL, 0.148 mol) and diisopropylamine tetrazolide (5.46 g, 0.3 eq.) was added. The mixture was stirred for 16 hours. The mixture was washed with saturated sodium bicarbonate (1 L) and the bicarbonate solution was back extracted with dichloromethane (500 mL). The combined organic layers were washed with brine (1 L) and the brine was back extracted with dichloromethane (100 mL). The combined organic layers were dried over sodium sulfate, filtered, and concentrated to a vol of about 200 mL. The resulting material was purified by silica gel column chromatography using hexane/ethyl acetate/triethyl amine 60/40/1. The product fractions were concentrated in vacuo, dissolved in acetonitrile (500 ml), filtered, concentrated in vacuo, and dried to a foam. The foam was chopped and dried for 24 hour to a constant weight to give 68.2 g (84%) of the title compound. 1H NMR: (CDCl$_3$) δ0.9–1.4 (m, 14H, 4×CH$_3$, 2×CH), 2.3–2.4 (t, 1H, CH$_2$CN), 2.6–2.7 (t, 1H, CH$_2$CN), 3.3–3.8 (m, 13H, 2×CH$_3$OAr, 5' CH$_2$, CH$_2$OP, C-5 CH$_3$), 4.2–4.3 (m, 1H, 4'), 4.35–5.0 (m, 1H, 3'), 4.9–5.2 (m, 1H, 2'), 6.0–6.1 (dd, 1H, 1'), 6.8–7.4 (m, 13H, DMT), 7.5–7.6 (d, 1H, C-6) , 8.8 (bs, 1H, NH). $^{31}$P NMR (CDCl$_3$); 151.468, 151.609, 151.790, 151.904.

EXAMPLE 5

1-(3',5'-di-O-acetyl-2-fluoro-β-D-erythro-pentofuranosyl)-5-methyluridine 1-(2-fluoro-β-D-erythro-pentofuranosyl)-5-methyluridine (22.4 g, 92 mmol, 85% purity), prepared as per the procedure of Example 2, was azeotroped with pyridine (2×150 mL) and dissolved in pyridine (250 mL). Acetic anhydride (55 mL, 0.58 mol) was added and the mixture was stirred for 16 hours. Methanol (50 mL) was added and stirring was continued for 30 minutes. The mixture was evaporated to a syrup. The syrup was dissolved in a minimum amount of methanol and loaded onto a silica gel column. Hexane/ethyl acetate, 1:1, was used to elute the product fractions. Purification gave 19.0 g (74%) of the title compound.

EXAMPLE 6

4-Triazine-1-(3',5'-di-O-acetyl-2-fluoro-β-D-erythro-pentofuranosyl)-5-methyluridine 1,2,4-Triazole (106 g, 1.53 mol) was dissolved in acetonitrile (150 mL) followed by triethylamine (257 mL, 1.84 mol). The mixture was cooled to between 0 and 10° C. using an ice bath. $POCl_3$ (34.5 mL, 0.375 mol) was added slowly via addition funnel and the mixture was stirred for an additional 45 minutes. In a separate flask, 1-(3',5'-Di-O-acetyl-2-fluoro-β-D-erythro-pentofuranosyl)-5-methyluridine (56.9 g, 0.144 mol) was dissolved in acetonitrile (150 mL). The solution containing the 1-(3',5'-Di-O-acetyl-2-fluoro-β-D-erythro-pentofuranosyl)-5-methyluridine was added via cannula to the triazole solution slowly. The ice bath was removed and the reaction mixture was allowed to warm to room temperature for 1 hour. The acetonitrile was removed in vacuo and the residue was partitioned between saturated sodium bicarbonate solution (400 mL) and dichloromethane (4×400 mL). The organic layers were combined and concentrated in vacuo. The resulting residue was dissolved in ethyl acetate (200 mL) and started to precipitate a solid. Hexanes (300 mL) was added and additional solid precipitated. The solid was collected by filtration and washed with hexanes (2×200 mL) and dried in vacuo to give 63.5 g which was used as is without further purification.

EXAMPLE 7

5-methyl-1-(2-fluoro-β-D-erythro-pentofuranosyl)-Cytosine

4-Triazine-1-(3',5'-di-O-acetyl-2-fluoro-β-D-erythro-pentofuranosyl)-Thymine (75.5 g, 0.198 mol) was dissolved in ammonia (400 mL) in a stainless steel bomb and sealed overnight. The bomb was cooled and opened and the ammonia was evaporated. Methanol was added to transfer the material to a flask and about 10 volumes of ethyl ether was added. The mixture was stirred for 10 minutes and then filtered. The solid was washed with ethyl ether and dried to give 51.7 g (86%) of the title compound.

EXAMPLE 8

4-N-Benzoyl-5-methyl-1-(2-fluoro-β-D-erythro-pentofuranosyl)-Cytosine 5-methyl-1-(2-fluoro-β-D-erythro-pentofuranosyl)-Cytosine (54.6 g, 0.21 mol) was suspended in pyridine (700 mL) and benzoic anhydride (70 g, 0.309 mol) was added. The mixture was stirred for 48 hours at room temperature. The pyridine was removed by evaporation and methanol (800 mL) was added and the mixture was stirred. A precipitate formed which was filtered, washed with methanol (4×50 mL), washed with ether (3×100 mL), and dried in a vacuum oven at 45° C. to give 40.5 g of the title compound. The filtrate was concentrated in vacuo and treated with saturated methanolic ammonia in a bomb overnight at room temperature. The mixture was concentrated in vacuo and the resulting oil was purified by silica gel column chromatography. The recycled starting material was again treated as above to give an additional 4.9 g of the title compound to give a combined 45.4 g (61%) of the title compound.

EXAMPLE 9

4-N-Benzoyl-5-methyl-1-(2-fluoro-5-O-dimethoxytrityl-β-D-erythro-pentofuranosyl)-Cytosine 4-N-Benzoyl-5-methyl-1-(2-fluoro-β-D-erythro-pentofuranosyl)-Cytosine (45.3 g, 0.124 mol) was dissolved in 250 ml dry pyridine and dimethoxytrityl chloride (46.4 g, 0.137 mol) was added. The reaction mixture was stirred at room temperature for 90 minutes and methanol (20 mL) was added. The mixture was concentrated in vacuo and partitioned between ethyl acetate (2×1 L) and saturated sodium bicarbonate (1 L). The ethyl acetate layers were combined, dried over magnesium sulfate and evaporated in vacuo. The resulting oil was dissolved in dichloromethane (200 mL) and purified by silica gel column chromatography using ethyl acetate/hexane/triethyl amine 50:50:1. The product fractions were pooled concentrated in vacuo dried to give 63.6 g (76.6%) of the title compound.

EXAMPLE 10

4-N-Benzoyl-5-methyl-1-(2-fluoro-3-O-N,N-diisopropylamino-2-cyanoethylphosphite-5-O-dimethoxytrityl-β-D-erythro-pentofuranosyl)-Cytosine 4-N-Benzoyl-5-methyl-1-(2-fluoro-5-O-dimethoxytrityl-β-D-erythro-pentofuranosyl)-Cytosine (61.8 g, 92.8 mmol) was stirred with dichloromethane (300 mL), 2-cyanoethyl N,N,N',N'-tetraisopropylphosphorodiamidite (40.9 mL, 0.130 mol) and diisopropylamine tetrazolide (4.76 g, 0.3 eq.) at room temperature for 17 hours. The mixture was washed with saturated sodium bicarbonate (1 L) and the bicarbonate solution was back extracted with dichloromethane (500 mL). The combined organic layers were washed with brine (1 L) and the brine was back extracted with dichloromethane (100 mL). The combined organic layers were dried over sodium sulfate, filtered, and concentrated to a vol of about 200 mL. The resulting material was purified by silica gel column chromatography using hexane/ethyl acetate/triethyl amine 60/40/1. The product fractions were concentrated in vacuo, dissolved in acetonitrile (500 ml), filtered, concentrated in vacuo, and dried to a foam. The foam was chopped and dried for 24 hours to a constant weight to give 72.4 g (90%) of the title compound. 1H NMR: ($CDCl_3$) δ1.17–1.3 (m, 12H, 4×$CH_3$), 1.5–1.6 (m, 2H, 2×CH), 2.3–2.4 (t, 1H, $CH_2CN$), 2.6–2.7 (t, 1H, $CH_2CN$), 3.3–3.9 (m, 13H, 2×$CH_3OAr$, 5' $CH_2$, $CH_2OP$, C-5 $CH_3$), 4.2–4.3 (m, 1H, 4'), 4.3–4.7 (m, 1H, 3'), 5.0–5.2 (m, 1H, 2'), 6.0–6.2 (dd, 1H, 1'), 6.8–6.9 (m, 4H, DMT), 7.2–7.6 (m, 13H, DMT, Bz), 7.82–7.86 (d, 1H, C-6), 8.2–8.3 (d, 2H, Bz). $^{31}P$ NMR ($CDCl_3$); bs, 151.706; bs, 151.941.

EXAMPLE 11

1-(2,3-di-O-Butyltin-β-D-erythro-Pentofuranosyl)-5-Methyluridine

5-Methyl uridine (7.8 g, 30.2 mmol) and dibutyltin oxide (7.7 g, 30.9 mmol) were suspended in methanol (150 mL) and heated to reflux for 16 hours. The reaction mixture was cooled to room temperature, filtered, and the solid washed with methanol (2×150 mL). The resulting solid was dried to give 12.2 g (80.3%) of the title compound. This material was used without further purification in subsequent reactions. NMR was consistent with structure.

EXAMPLE 12

1-(2-O-Propyl-β-D-erythro-Pentofuranosyl)-5-Methyluridine 1-(2,3-di-O-butyltin-β-D-erythro-pentofuranosyl)-5-methyluridine (5.0 g, 10.2 mmol) and iodopropane (14.7 g, 72.3 mmol) were stirred in DMF at 100° C. for 2 days. The reaction mixture was cooled to room temperature and filtered and concentrated. The residual DMF was coevaporated with acetonitrile. After drying the residue there was obtained 2.40 g (78%) of the title compound and the 3'-O-propyl isomer as a crude mixture. This material was used without further purification in subsequent reactions.

EXAMPLE 13

1-(2-O-Propyl-5-O-Dimethoxytrityl-β-D-erythro-Pentofuranosyl)-5-Methyluridine 1-(2-O-Propyl-β-D-erythro-pentofuranosyl)-5-methyluridine and the 3'-O-propyl isomer as a crude mixture (2.4 g, 8.4 mmol) was coevaporated with pyridine (2×40 mL) and dissolved in pyridine (60 mL). The solution was stirred at room temperature under argon for 15 minutes and dimethoxytrityl chloride (4.27 g, 12.6 mmol) was added. The mixture was checked periodically by tlc and at 3 hours was completed. Methanol (10 mL) was added and the mixture was stirred for 10 minutes. The reaction mixture was concentrated in vacuo and the resulting residue purified by silica gel column chromatography using 60:40 hexane/ethyl acetate with 1% triethylamine used throughout. The pooling and concentration of appropriate fractions gave 1.32 g (26%) of the title compound.

EXAMPLE 14

1-(2-O-Propyl-3-O-N,N-Diisopropylamino-2-Cyanoethylphosphite-5-O-Dimethoxytrityl-β-D-erythro-Pentofuranosyl)-5-Methyluridine 1-(2-O-Propyl-5-O-dimethoxytrityl-β-D-erythro-pentofuranosyl)-5-methyluridine (50.0 g, 86 mmol), 2-cyanoethyl-N,N,N',N'-tetra-isopropylphosphorodiamidite (38 mL, 120 mmol), and diisopropylamine tetrazolide (4.45 g, 25.8 mmol) were dissolved in dichloromethane (500 mL) and stirred at room temperature for 40 hours. The reaction mixture was washed with saturated sodium bicarbonate solution (2×400 mL) and brine (1×400 mL). The aqueous layers were back extracted with dichloromethane. The dichloromethane layers were combined, dried over sodium sulfate, filtered, and concentrated in vacuo. The resultant residue was purified by silica gel column chromatography using ethyl acetate/hexane 40:60 and 1% triethylamine. The appropriate fractions were pooled, concentrated, and dried under high vacuum to give 43 g (67%).

EXAMPLE 15

1-(2-O-Propyl-3-O-Acetyl-5-O-Dimethoxytrityl-β-D-erythro-Pentofuranosyl)-5-Methyluridine 1-(2-O-Propyl-5-dimethoxytrityl-β-D-erythro-pentofuranosyl)-5-methyluridine (10.0 g, 16.6 mmol) was dissolved in pyridine (50 mL) and acetic anhydride (4.7 ml, 52.7 mmol) was added. The reaction mixture was stirred for 18 hours and excess acetic anhydride was neutralized with methanol (10 mL). The mixture was concentrated in vacuo and the resulting residue dissolved in ethyl acetate (150 mL). The ethyl acetate was washed with saturated NaHCO$_3$ (150 mL) and the saturated NaHCO$_3$ wash was back extracted with ethyl acetate (50 mL). The ethyl acetate layers were combined and concentrated in vacuo to yield a white foam 11.3 g. The crude yield was greater than 100% and the NMR was consistent with the expected structure of the title compound. This material was used without further purification in subsequent reactions.

EXAMPLE 16

1-(2-O-Propyl-3-O-Acetyl-5-O-Dimethoxytrityl-β-D-erythro-Pentofuranosyl)-4-Triazolo-5-Methylpyrimidine Triazole (10.5 g, 152 mmol) was dissolved in acetonitrile (120 ml) and triethylamine (23 mL) with stirring under anhydrous conditions. The resulting solution was cooled in a dry ice acetone bath and phosphorous oxychloride (3.9 mL, 41 mmol) was added slowly over a period of 5 minutes. The mixture was stirred for an additional 10 minutes becoming a thin slurry indicative of product formation. 1-(2-O-Propyl-3-O-acetyl-5-O-dimethoxytrityl-β-D-erythro-pentofuranosyl)-5-methyluridine (11.2 g, 165 mmol) was dissolved in acetonitrile (150 mL) and added to the slurry above, maintaining dry ice acetone bath temperatures. The reaction mixture was stirred for 30 minutes and then allowed to warm to room temperature and stirred for an additional 2 hours. The mixture was placed in a freezer at 0° C. for 18 hours and then removed and allowed to warm to room temperature. Tlc in ethyl acetate/hexane 1:1 of the mixture showed complete conversion of the starting material. The reaction mixture was concentrated in vacuo and redissolved in ethyl acetate (300 mL) and extracted with saturated sodium bicarbonate solution (2×400 mL) and brine (400 mL). The aqueous layers were back extracted with ethyl acetate (200 mL). The ethyl acetate layers were combined, dried over sodium sulfate, and concentrated in vacuo. The crude yield was 11.3 g (95%). The NMR was consistent with the expected structure of the title compound. This material was used without further purification in subsequent reactions.

EXAMPLE 17

1-(2-O-Propyl-5-O-Dimethoxytrityl-β-D-erythro-Pentofuranosyl)-5-Methylcytidine 1-(2-O-Propyl-3-O-acetyl-5-O-dimethoxytrityl-β-D-erythro-pentofuranosyl)-4-triazolo-5-methylpyrimidine (11.2 g, 16.1 mmol) was dissolved in liquid ammonia (50 mL) in a 100 mL bomb at dry ice acetone temperatures. The bomb was allowed to warm to room temperature for 18 hours and then recooled to dry ice acetone temperatures. The bomb contents were transferred to a beaker and methanol (50 mL) was added. The mixture was allowed to evaporate to near dryness. Ethyl acetate (300 mL) was added and some solid was filtered off prior to washing with saturated sodium bicarbonate solution (2×250 mL). The ethyl acetate layers were dried over sodium sulfate, filtered, combined with the solid previously filtered off, and concentrated in vacuo to give 10.1 g of material. The crude yield was greater than 100% and the NMR was consistent with the expected structure of the title compound. This material was used without further purification in subsequent reactions.

EXAMPLE 18

1-(2-O-Propyl-5-O-Dimethoxytrityl-β-D-erythro-Pentofuranosyl)-4-N-Benzoyl-5-Methylcytidine 1-(2-O-Propyl-5-O-dimethoxytrityl-β-D-erythro-pentofuranosyl)-5-methylcytidine (7.28 g, 10.1 mmol) and benzoic anhydride (4.5 g, 20 mmol) were dissolved in DMF (60 mL) and stirred at room temperature for 18 hours. The reaction mixture was concentrated in vacuo and redissolved in ethyl acetate (300 mL). The ethyl acetate solution was washed with saturated sodium bicarbonate solution (2×400 mL), dried over sodium sulfate, filtered, and concentrated in vacuo. The residue was purified by silica gel column chromatography using ethyl acetate/hexane 1:2 and 1% triethylamine. The appropriate fractions were pooled, concentrated, and dried under high vacuum to give 5.1 g (59% for 4 steps starting with the 1-(2-O-Propyl-dimethoxytrityl-β-D-erythro-pentofuranosyl)-5-methyluridine).

EXAMPLE 19

1-(2-O-Propyl-3-O-N,N-Diisopropylamino-2-Cyanoethylphosphite-5-O-Dimethoxytrityl-β-D-erythro-Pentofuranosyl)-4-N-Benzoyl-5-Methylcytidine 1-(2-O-Propyl-5-O-dimethoxytrityl-β-D-erythro-pentofuranosyl)-4-N-benzoyl-5-methylcytidine (5.0 g, 7 mmol), 2-cyanoethyl-N,N,N',N'-tetra-isopropylphosphorodiamidite (3.6 mL, 11.3 mmol), and diisopropylaminotetrazolide (0.42 g, 2.4 mmol) were dissolved in dichloromethane (80 mL) and stirred at room temperature for 40 hours. The reaction mixture was washed with saturated sodium bicarbonate solution (2×40 mL) and brine (1×40 mL). The aqueous layers were back extracted with dichloromethane. The dichloromethane layers were combined, dried over sodium sulfate, filtered, and concentrated in vacuo. The resultant residue was purified by silica gel column chromatography using ethyl acetate/hexane 40:60 and 1% triethylamine. The appropriate fractions were pooled, concentrated, and dried under high vacuum to give 7.3 g (98%).

EXAMPLE 20

2'-O-Methyl-5-methyluridine

Procedure 1

Crude 2,2'-anhydro-5-methyluridine (10.0 g, 0.0416 mol) was dissolved in methanol (80 mL) in a stainless steel bomb (100 mL capacity). Trimethyl borate (5.6 mL, 0.049 mol) was added (Note 1). The bomb was sealed and placed in an oil bath at 150° C. which generated a pressure of about 5 atm. After 40 h, the bomb was cooled in ice, opened and the contents concentrated under reduced pressure to a tan foam, 12 g. NMR of the crude was consistent with the product contaminated with impurities in the starting material and a trace of thymine and starting material (Note 2). The crude product was used as is for the next step.

Note that Trialkyl borates can be conveniently generated by adding solutions (eg 1M in THF) of borane to the desired alcohol and allowing the resulting hydrogen gas to evolve.) Also note that the nucleoside can be purified at this point by column chromatography using a gradient of methanol in ethyl acetate (0–10%) and crystallizing the product from absolute ethanol to give white needles, mp 192°–193° (mp 197°–198°). Literature reference for the melting point of this compound is contained in E. Ootsuka, H. Inoue, Japanese Patent 89-85456, 4 Apr., 1989.

Procedure 2

Pure 2,2'-anhydro-5-methyluridine (1.0 g, 4.16 mmol) and trimethylborate (0.56 mL, 4.9 mmol) was dissolved in methanol (20 mL) in a stainless steel bomb (100 mL). The bomb was placed in an oil bath at 150° C. After 80 h, TLC indicating the reaction to be mostly complete. The solvent was removed yielding a white foam. NMR indicated product to starting material ratio of 93:7 with no other impurities noted. The residue was purified by silica gel column chromatography using a methanol gradient in ethyl acetate (0–10%) yielding 850 mg (75%) of pure product and 250 mg of still contaminated product. An analytically pure sample was prepared for NMR. $^1$H NMR (DMSO-d$_6$): δ1.79 (s, 3H, 5-CH$_3$), 3.35 (s, 3H, OCH$_3$), 3.5–3.7 (m, 2H, H-5'), 3.7–3.9 (m, 2H, H-3',4'), 4.15 (m, 1H, H-2'), 5.17 (m, 2H, 3',5'-OH), 5.87 (d, J=5Hz, 1H, H-1'), 7.80 (s, 1H, H-6), 11.37 (br s, 1H, N-H). Anal. Calcd for $C_{11}H_{16}N_2O_6$ (272.26): C, 48.52; H, 5.92; N, 10.29. Found: C, 48.56; H, 5.88; N, 10.22.

Procedure 3

Pure 2,2'-anhydro-5-methyluridine (10.0 g, 41.6 mmol), trimethyl borate (10.0 mL, 85 mmol), NaHCO$_3$ (30 mg), and MeOH (70 mL) were heated in a pressure bomb to about 175° C. for 60 hours. The pressure bomb was cooled to room temperature and the contents were evaporated to a white foam in vacuo. The resulting foam was triturated with ether (100 mL) and the resulting white solid was collected by filtration and dried in vacuo at 50° C. for four hours to give the title compound 10.7 g (100%). NMR analysis shows about a 3% impurity identified as the starting material thymine and ara-5-methyl-uridine.

EXAMPLE 21

5'-O-Dimethoxytriphenylmethyl-2'-O-methyl-5-methyluridine

Crude 2'-O-methyl-5-methyl uridine (12 g) was coevaporated in pyridine (2×50 mL) and dissolved in dry pyridine (50 mL). Dimethoxytriphenylmethyl chloride (18.1 g, 0.054 mol) was added. the flask was stoppered and allowed to stand for 45 min at room temperature. Methanol (10 mL) was added to quench the reaction and the solution was concentrated under reduced pressure to an oil. The residue was partitioned between ethyl acetate (2×400 mL) and saturated sodium bicarbonate solution (500 mL). The organic layers were combined, dried (sodium sulfate), filtered and concentrated to a yellow foam. The foam was dissolved in methylene chloride (60 mL) and put onto a silica gel column (300 g) and eluted with ethyl acetate-hexanes-triethylamine, 60:40:1. The product containing fractions were combined, concentrated and coevaporated with dry acetonitrile (2×50 mL). The resulting residue was dried at 1 mm Hg for 24 h to a crisp white foam, 17.0 g (60.4% in three steps from 5-methyluridine).

EXAMPLE 22

2,3,5-Tri-O-Benzoyl-2-Thio-5-Methyl Uridine

In a 250 ml 3 neck round bottomed flask 1-O-acetyl-2,3,5 tri-O-benzoyl ribose (0.500 g, 1 mmol) and 5-methyl-2-thio-uracil (0.156 g, 1.1 mmol) was dried under vacuum overnight. These components were dissolved in 10 mL of dry acetonitrile and heated to 80° C. To this warm solution was added N-O-Bis(trimethyl silyl)acetamide (0.509 g, 2.5 mmol) and the reaction stirred for 1 hr at 80° C. The reaction mixture was removed from the heat and allowed to cool to room temperature, and trimethyl silyl triflate (0.334 g, 1.5 mmol) was added dropwise. The reaction mixture was then heated to 50° C. and stirred for 4 hours. The reaction mixture was checked by TLC using ethyl acetate/hexane 1:1, which showed the reaction had gone to completion. The solution was cooled to room temperature and partitioned between 50 mL of dichloromethane and 50 mL of saturated sodium bicarbonate solution. The aqueous phase was extracted two more times with dichloromethane and the organic layers combined, dried with magnesium sulfate and concentrated to a pale yellow foam. This foam was used without further purification.

EXAMPLE 23

2-Thio-5-Methyl Uridine

The crude 2,3,5-tri-O-benzoyl-2-thio-5-methyl uridine (20 g, 37 mmoles) was dissolved in 500 mL of methanol. To this solution was added sodium methoxide (2.0 g, 37 mmoles) and the reaction stirred for 2 hours. The reaction was checked by TLC using ethyl acetate/hexane 1:1 and ethyl acetate/methanol 9:1, which showed the reaction had gone to completion. Dowex 50 H$^+$ resin was added until the solution was neutral by pH paper and the resin filtered. The resin was then washed with 100 ml of additional methanol and the combined filtrates were concentrated to give the title compound 8.5 g, (84%) as a pale yellow foam.

EXAMPLE 24

2'-O-Methyl-5-Methyl-2-Thiouridine

To a stirred solution of 5-methyl-2-thiouridine (0.500 g, 1.8 mmol) in DMF (10 ml) is added dibutyltin oxide (0.500 g, 2.0 mmol), tetrabutyl ammonium iodide (0.738 g, 2 mmol), and methyl iodide (1.022 g, 7.2 mmol). The reaction flask is sealed and heated at 50° C. for 16 hours. The mixture is cooled and another portion of methyl iodide is added (1.022 g, 7.2 mmol) and the reaction heated for an additional 16 hours. At the end of this time, the reaction mixture is cooled to room temperature and diluted with methylene chloride and chromatographed using a methylene chloride/methanol gradient. The appropriate fractions are collected and concentrated to give 2'-O-methyl-5-methyl-2-thiouridine.

EXAMPLE 25

2'-O-propyl 5-methyl-2-thiouridine

The title compound is prepared as per the procedures of Example 24 by substituting propyl iodide (1.22 g, 7.2 mmoles) in place of methyl iodide.

EXAMPLE 26

2'-O-phthalimidopropyl-5-methyl-2-thiouridine

The title compound is prepared as per the procedures of Example 24 by substituting bromo-propyl phthalimide (0.67 g, 2.5 mmoles) in place of methyl iodide, with an additional (0.300 g) added on the second day.

EXAMPLE 27

5'-O-Dimethoxytrityl-2'-O-Propylamine-5-Methyl-2-Thiouridine

2'-O-Phthalimidopropyl-5-methyl-2-thiouridine (2.6 g, 3.6 mmol) is dissolved in dry pyridine and co-evaporated twice. The resulting foam is dissolved in 25 mL of dry pyridine and dimethoxy-trityl chloride (1.8 g, 5.5 mmol) is added followed by 4,4-dimethylaminopyridine (0.050 g, 0.4 mmol). The reaction is allowed to stir overnight at room temperature. To the reaction mixture is added 1 mL of methanol. The solution is partitioned between 75 mL of saturated sodium bicarbonate and 50 mL of chloroform. The aqueous layer is extracted with two additional portions of chloroform and the organic layers combined and dried with magnesium sulfate. After removal of the drying agent via filtration the filtrate is concentrated to an orange oil and purified by silica gel column chromatography using methanol/chloroform gradient with 0.5% pyridine added to neutralize the silica gel.

EXAMPLE 28

5'-O-Dimethoxytrityl-2'-O-Propylamine-5-Methyl-2S-toluoyl-2-Thiouridine

5'-O-Dimethoxytrityl-2'-O-propylamine-5-methyl-2-thiouridine (1 g, 1.6 mmol) is dissolved in DMF and cooled to 0° C. To this solution is added triethyl amine (0.300 g, 3 m.mol) followed by toluoyl chloride (0.300 g, 1.92 mmol) dropwise over 5 minutes. The reaction is then allowed to warm to room temperature and stirred overnight. When complete the reaction is quenched with methanol and concentrated to an oil. The oil is then partitioned between 250 mL of a solution of saturated sodium bicarbonate/chloroform 1:1. The aqueous layer is extracted with two additional 75 mL portions of chloroform, and the organic layers are dried and concentrated to an oil. The protected nucleoside is purified by silica gel column chromatography using a hexane/ethyl acetate gradient. The desired product is collected as a mixture of N-3 toluoyl and S-2 Toluoyl compounds. This mixture is used for the phosphytilation procedure.

EXAMPLE 29

5'-O-Dimethoxytrityl-2'-O-Propylamine-3'-O-[(N,N-diisopropylamino)-2-cyanoethoxyphosphite]-5-Methyl-2-S-toluoyl-2-Thiouridine To a solution of 5'-O-dimethoxytrityl-2'-O-propylamine-5-methyl-2-S-toluoyl-2-thiouridine (16.01 g, 22 mmol) and diisopropylethylamine (10 ml) in THF (200 ml), at 0° C., is added chloro-β-cyanoethoxy-N,N-diisopropylaminophosphine (5.6 ml, 25mmol). The reaction mixture is stirred at room temperature for 20 hours. The reaction is concentrated and the residue purified by silica gel column chromatography. Elution with an ethyl acetate/hexane gradient while maintaining 1% triethylamine, pooling of appropriate fractions and evaporation will give the title compound.

EXAMPLE 30

2'-O-Aminopropyl-5-Methyl-2-Thiouridine

2'-O-Phthalimidopropyl-5-methyl-2-thiouridine (5.0 g, 15.8 mmol) is dissolved in 100 ml methanol in a 500 ml flask. Hydrazine (2.02 g, 63.2 mmol) is added and the mixture is heated to reflux (60°–65° C.) with stirring for 14 hours. The solvent is evaporated in vacuo and the residue is dissolved in dichloromethane (150 ml) and extracted twice with an equal volume NH$_4$OH. The organic layer is evaporated to yield the crude product. NMR is used to assay product purity. The product is used in subsequent reactions without further purification.

EXAMPLE 31

2'-O-Trifluoroacetylaminopropyl-5-Methyl-2-Thiouridine

2'-O-Aminopropyl-5-methyl-2-thiouridine is dissolved in MeOH and 5 equivalents of triethylamine are added followed by 10 equivalents of ethyl trifluoroacetate. The title compound is isolated after purification.

EXAMPLE 32

2'-O-Trifluoroacetylaminopropyl-5'-O-Dimethoxytrityl-5-Methyl-2-Thiouridine

2'-O-Trifluoroacetylaminopropyl-5-methyl-2-thiouridine (2.5 g, 3.6 mmol) is dissolved in dry pyridine and co-evaporated twice. The resulting yellow foam is dissolved in 25 mL of dry pyridine and dimethoxytrityl chloride (1.8 g, 5.5 mmol) is added followed by 4,4-dimethylaminopyridine (0.050 g, 0.4 mmol). The reaction is allowed to stir overnight at room temperature. To the reaction mixture is added 1 mL of methanol. The solution is partitioned between 75 mL of saturated sodium bicarbonate and 50 mL of chloroform. The aqueous layer is extracted with two additional portions of chloroform and the organic layers combined and dried with magnesium sulfate. After removal of the drying agent via filtration the filtrate is concentrated to an oil and purified by silica gel column chromatography using methanol/chloroform gradient with 0.5% pyridine added to neutralize the silica gel to give the title compound.

EXAMPLE 33

2'-O-Trifluoroacetylaminopropyl-3'-O-[(N,N-diisopropylamino)-2-cyanoethoxyphosphite]-5'-O-Dimethoxytrityl-5-Methyl-2-Thiouridine The title compound is prepared as per the procedure of Example 29 using the title compound from Example 32.

EXAMPLE 34

5'-O-Dimethoxytrityl-2-Thio-5-Methyl Uridine

2-Thio-5-methyl uridine (1 g, 3.6 mmol) was dissolved in dry pyridine and co-evaporated twice. The resulting yellow foam was dissolved in 25 mL of dry pyridine and dimethoxy-trityl chloride (1.8 g, 5.5 mmol) was added followed by 4,4-dimethylaminopyridine (0.050 g, 0.4 mmol). The reaction was allowed to stir overnight at room temperature. To the reaction mixture was added 1 mL of methanol. The solution was partitioned between 75 mL of saturated sodium bicarbonate and 50 mL of chloroform. The aqueous layer was extracted with two additional portions of chloroform and the organic layers combined and dried with magnesium sulfate. After removal of the drying agent via filtration the filtrate was concentrated to an orange oil and purified by silica gel column chromatography using methanol/chloroform gradient with 0.5% pyridine added to neutralize the silica gel.

EXAMPLE 35

5'-O-Dimethoxytrityl-3'-t-butyldimethylsilyl-5-Methyl-2-thiouridine

5'-O-Dimethoxytrityl-2-thio-5-methyl uridine (1 g, 1.73 mmol) was co-evaporated twice with dry DMF and then dissolved in dry DMF and imidazole (0.141 g, 2.08 mmol) was added followed by (0.313 g, 2.08 mmol) of t-butyldimethylsilyl chloride. The reaction mixture was stirred overnight. The reaction was checked by TLC using ethyl acetate/hexane 1:1, which showed the reaction had gone to completion. The reaction mixture was then poured into 5% sodium bicarbonate and extracted 3 times with chloroform. The combined organic solution was dried with magnesium sulfate and concentrated to an oil. The resulting oil was purified by silica gel column chromatography using a methanol/chloroform gradient isolating separately the 2' and 3' silyl protected nucleoside.

EXAMPLE 36

5'-O-Dimethoxytrityl-3'-t-Butyldimethylsilyl-2'-Methanesulfonyl-5-Methyl-2-Thiouridine 5'-O-Dimethoxytrityl-3'-t-butyldimethylsilyl-5-methyl-2-thiouridine (1.0 g, 1.45 mmoles) was dissolved in pyridine and cooled to 0° C. To this solution was added methanesulfonyl chloride (0.183 g, 1.6 mmoles) dropwise. The reaction was then allowed to stir until complete by TLC. The reaction mixture is neutralized with methanol and concentrated to an oil. The title compound is used as is for further reactions.

EXAMPLE 37

5'-DMT-3'-t-butyl dimethylsilyl-2,2' thio anhydro-5-methyl-2-thiouridine

The mesylated nucleoside found in Example 36 is treated at room temperature with 5 equivalents of sodium methoxide and allowed to stir until complete formation of the thioanhydro product. The solution is then neutralized with Dowex 50W ($H^+$ form), the resin filtered off and the resulting solution concentrated to give the title compound.

EXAMPLE 38

2'-Fluoro-3'-t-butyl dimethylsilyl-5'-DMT-5-methyl-2-thiouridine

The thioanhydronucleoside found in Example 37 was dissolved in anhydrous dioxane. To this solution was added 6 equivalents of HF/Pyridine complex and the reaction stirred until complete by TLC. The reaction mixture is then poured over an equal volume of ice and calcium carbonate is added until neutral. The solids are filtered off and the filtrate is concentrated. The residue is purified by silica gel column chromatography to give the title compound.

EXAMPLE 39

2'-Fluoro-3'-O-[(N,N-diisopropylamino)-2-cyanoethoxyphosphite]-5'-DMT-5-methyl-2-thiouridine 2'-Fluoro-3'-t-butyl dimethylsilyl-5'-DMT-5-methyl-2-thiouridine is treated as per the procedure of Example 29 to give the title compound.

EXAMPLE 40

2'-O-substituted oligoribonucleotides Nuclease Stability

The 2'-O-methyl phosphoramidites were purchased from Glen Research, Sterling, Va. The 2'-O-propyl and 2'-O- pentyl phosphoramidites were prepared as described in Lesnik, E. A., et.al., *Biochemistry*, 1993, 32, 7832–7838; Guinosso, et.al., *Nucleosides and Nucleotides,* 1991, 10, 259–262. CPG derivatized with 2'-O-substituted nucleosides was prepared as described by Damha, M. J., Giannaris, P. A. and Zabarylo, S. V., *Nucl. Acids Res.,* 1990, 18, 3813–3821. Other reagents for solid phase DNA synthesis were purchased from commercial sources. Oligomers were synthesized using solid-phase chemistries on an ABI model 380B DNA synthesizer. Oligomers were purified by polyacrylamide gel electrophoresis, followed by desalting with Polypak cartridges (Glen Research, Sterling, Va). Oligoribonucleotides were 5' end labeled using [g-$^{32}$P]ATP and T4 polynucleotide kinase. After the labeling reaction, the T4 polynucleotide kinase was heat inactivated at 95° C. for 3 minutes and oligomers were used without any further purification.

The oligoribonucleotide sequences synthesized for nuclease resistance studies are shown in Table 1. Incorporation of the different 2'-O-alkyl moieties into the 12-mer series was verified by electrospray mass spectroscopy and the calculated and measured masses agreed to within 0.01%.

Snake venom phosphodiesterase ($\mu$gSB, Cleveland, Ohio) assays were performed using 1 $\mu$M oligomer at 37° C. in a buffer of 50 mM Tris-HCL, pH 8.5, 72 mM NaCl, and 14 mM MgCl$_2$ at an enzyme concentration of $5\times10^{-2}$ $\mu$g/ml or $5\times10^{-3}$ $\mu$g/ml. The enzyme was shown to maintain its activity under these conditions for at least 24 hours. Nuclease S1 (Gibco BRL, Gaithersburg, Md.) assays were performed using 1 $\mu$M oligomer at 37° C. in 30 mM NaOAc pH 4.5, 50 mM NaCl, and 1 mM ZnCl$_2$. Nuclease S1 was used at either 1.9 $\mu$g/ml or $1.9\times10^6$ $\mu$g/ml. Aliquots of the nuclease stability reactions were removed at the indicated times, quenched by addition to an equal volume of 80% formamide gel loading buffer containing tracking dyes, heated for 2 minutes at 95° C. and then stored at −20° C. until analysis by denaturing polyacrylamide electrophoresis. Quantitation was performed on a Molecular Dynamics PhosphorImager (Molecular Dynamics, Sunnyvale, Calif.).

TABLE 1

Modified oligoribonucleotide sequences used in nuclease studies

| 2'-O-substitution | backbone | 17-mer | 12-mer |
|---|---|---|---|
| 2'-deoxy | P=O | SEQ ID NO: 1 | SEQ ID NO: 6 |
| methyl | P=O | SEQ ID NO: 2 | SEQ ID NO: 7 |
| propyl | P=O | SEQ ID NO: 3 | SEQ ID NO: 8 |
| pentyl | P=O | SEQ ID NO: 4 | SEQ ID NO: 9 |
| 2'-deoxy | P=S | SEQ ID NO: 5 | SEQ ID NO: 10 |
| 17-mer: | 2'-deoxy (P=O) | 5' GGA CCG AAA GGT ACG AG 3' | |
| | methyl | 5' GGA CCG AAA GGU ACG AG 3' | |
| | propyl | 5' GGA CCG AAA GGU ACG AG 3' | |
| | pentyl | 5' GGA CCG AAA GGU ACG AG 3' | |
| | 2'-deoxy (P=S) | 5' GGA CCG AAA GGT ACG AG 3' | |
| 12-mer: | all | 5' CUA AGC AUG UCA 3' | | underlined = 2'-modified residues

The nuclease stability of the 17-mer series was examined using snake venom phosphodiesterase. The times required to reduce the quantity of full length material to 50% of its initial value ($t_{1/2}$) are listed in Table 4. Relative nuclease stability was calculated by dividing the observed $t_{1/2}$ value by the $t_{1/2}$ time of the unmodified compound. At an enzyme concentration of $5\times10^{-3}$ $\mu$g/ml, both the 2'-O-methyl and 2'-O-propyl analogs in the 17-mer series were 74-fold more stable than the unmodified control. The enzyme concentration was increased in an attempt to discriminate nuclease stability differences between the 2'-O-methyl and 2'-O-propyl analogs in this series. Performing the SVPD assay at an enzyme concentration of $5\times10^{-2}$ $\mu$g/ml resulted in 50% degradation of full-length 2'-deoxy phosphodiester oligomer in approximately 2.5 minutes. Under identical reaction conditions, the 2'-O-methyl phosphodiester, 2'-O-propyl phosphodiester, and 2' deoxy phosphorothioate analogs were 120-, 160-, and 350-fold more stable than the 2'-deoxy phosphodiester control (Table 2). Denaturing polyacrylamide gel analysis of these analogs indicated that degradation of the fully modified oligoribonucleotides does not proceed significantly beyond the first few 3'-nucleotides while the unmodified oligomer showed a ladder of degradation products. Qualitatively, the analyses suggest that the 2'-O-pentyl analog is even more resistant to exonuclease degradation than the 2'-O-methyl or 2'-O-propyl oligomers (data not shown). Quantitative analysis of the 2'-O-pentyl analog has been difficult for two reasons. First, the 2'-O-pentyl oligomers appear to be a poor substrates for polynucleotide kinase resulting in inefficient labeling. Second, quite often the majority of the labeled 2'-O-pentyl oligomer is trapped at the top of the gel. For this series of 17-mers, the order of stability appears to be: 2'-deoxy phosphorothioate≧2'-O-pentyl phosphodiester>2'-O-propyl phosphodiester>2'-O-methyl phosphodiester>2'-deoxy phosphodiester.

The relative nuclease stability of the 12-mer series was also determined using snake venom phosphodiesterase. This 12-mer series contains 2'-O-alkyl sugar modifications at every position, including the 3' terminal residue. The 2'-O-methyl phosphodiester, 2'-O-propyl phosphodiester, and 2' deoxy phosphorothioate analogs were 7-, 10-, and 89-fold more stable than the unmodified control (Table 2). The stability observed for the fully modified 2'-O-pentyl 12-mer oligoribonucleotide is qualitatively the same as for the 17-mer 2'-O-pentyl analog. The order of stability was the same as the 17-mer series. However, in contrast to the abbreviated degradation pattern of the 17-mer 2'-O-alkyl analogs, the 12-mer series exhibited a ladder of degradation products (data not shown). The rank order of stability of the 12-mers is identical to the 17-mers, but quantitative relative stabilities differ in the two series. The 2'-O-methyl and 2'-O-propyl analogs in the 12-mer series are 3- to 10-fold more resistant to snake venom phosphodiesterase than the unmodified control, and in the 17-mer series, these analogs exhibit 70- to 160-fold increase in stability relative to the unmodified control.

The stability of the 12-mer series of 2'-O-modified oligomers was also investigated using S1 nuclease, a single-stranded endonuclease. At an enzyme concentration of 1.9 $\mu$g/ml, no degradation of the 2'-O-methyl phosphodiester or 2'-O-propyl phosphodiester 12-mers is observed. Under the same conditions, the 2' deoxy phosphodiester and the 2' deoxy phosphorothioate analog have $t_{1/2}$'s of 2 and 13 minutes respectively (Table 2). Differences in the stability of 2'-O-methyl vs. the 2'-O-propyl modification were observed at a $10^5$ fold higher S1 nuclease concentration. At an enzyme concentration of $1.9\times10^5$ $\mu$g/ml, the $t_{1/2}$ of the 2'-O-methyl analog is 90 minutes, while no degradation of the 2'-O-propyl oligomer was observed.

TABLE 2

2'-O-modified oligoribonucleotide half lives with S1 nuclease and Snake Venom Phosphodiesterase.

| Oligomer SEQ ID NO: | $t_{1/2}$(min.) (5 × 10$^{-3}$ μg/ml) | Rel $t_{1/2}$ | $t_{1/2}$(min.) (5 × 10$^{-2}$ μg/ml) | rel. $t_{1/2}$ |
|---|---|---|---|---|
| Snake Venom Phosphodiesterase (12-mer series) | | | | |
| 6 | 12.0 | 1.0 | 1.5 | 1.0 |
| 7 | 38.0 | 3.2 | 11.0 | 7.3 |
| 8 | 68.0 | 5.7 | 15.0 | 10.0 |
| 11[2] | >68.0 | >5.7 | ND[3] | — |
| 10 | 975 | 81.3 | 133 | 88.7 |
| Snake Venom Phosphodiesterase (17-mer series) | | | | |
| 1 | 27.0 | 1.0 | 2.5 | 1.0 |
| 2 | 2000 | 74 | 300 | 120 |
| 3 | 2000 | 74 | 400 | 160 |
| 5 | no degradation | — | 875 | 350 |
| S1 Nuclease (12-mer series) | | | | |
| 6 | 2.0 | 1.0 | <1.0 | 1.0 |
| 7 | no degradation | — | 90 | >90 |
| 8 | no degradation | — | no degradation | — |
| 10 | 13.0 | 6.5 | <1.0 | — |

[1]Sequences and modifications are given in Table 1.
[2]This oligomer is a fully modified 2'-O-pentyl 12-mer, except the 5' residue is a 2'-deoxy C.
ND[3] = not determined

EXAMPLE 41

Determination of Hybridization Stability

Absorbance vs. temperature curves of duplexes were measured at 4 mM strand concentration (duplexes) or 6 mM strand concentration (single stranded studies) in 100 mM Na$^+$, 10 mM phosphate, 0.1 mM EDTA, pH 7 as described in Monia, B. P., et.al., *J. Biol. Chem.*, 1992, 267, 19954–19962. The melting temperature ($T_m$'s) and free energies of duplex formation were obtained from fits of data to a two state model with linear sloping baselines (Freier, S. M., Albergo, D. D., and Turner, D. H., *Biopolymers*, 1983, 22, 1107–1131). Free energies of duplex formation are a more valid measure of thermodynamic stability than $T_m$ as shown in Freier, S. M., et.al., *Gene Regulation: Biology of Antisense RNA and DNA*, C. F. Fox, Editor, Raven Press, New York, 1, 1992, pp. 95–107. Experimental errors, however, were larger for DG°$_{37}$ than for $T_m$. Therefore, we report $T_m$ values in Table 3.

TABLE 3

$T_m$'s of oligoribonucleotides containing uniform 2'-substitutions[1]

| modification | P=O[1] $T_m$ 15-mers | P=O[1] $T_m$ 17-mers | single stranded[3] $T_m$ 17-mers | P=S[1] $T_m$ 18-mers |
|---|---|---|---|---|
| 2'-deoxy | 45.1 | 56.5 | 67.9(PO), 57.6(PS) | 55.3 |
| 2'-O-methyl | 62.8 | 79.6 | 73.4(PO) | 80.9 |
| 2'-O-propyl | 58.5 | 74.8 | 77.8(PO) | 78.3 |
| 2'-O-pentyl | 45.9 | 61.8 | ND[2] | 54.2 |
| RNA | 59.2 | 74.5 | 68.6(PO) | ND[2] |

TABLE 3-continued $T_m$'s of oligoribonucleotides containing uniform 2'-substitutions[1]

Sequences studied:

| SEQ ID NO: | 15-mers | sequence |
|---|---|---|
| 12 | 2'-deoxy | CoGoAoCoToAoToGoCoAoAoGoToAoC |
| 13 | methy | CoGoAoCoToAoToGoCoAoAoGoToAoC |
| 14 | propyl | CoGoAoCoToAoToGoCoAoAoGoToAoC |
| 15 | pentyl | CoGoAoCoToAoToGoCoAoAoGoToAoC |
| 16 | RNA | CoGoAoCoToAoToGoCoAoAoGoToAoC |
| | 17-mers | |
| 17 | 2'-deoxy | GoGoAoCoCoGoGoAoAoGoGoToAoCoGoAoG |
| 18 | methy | GoGoAoCoCoGoGoAoAoGoGoUoAoCoGoAoG |
| 19 | propyl | GoGoAoCoCoGoGoAoAoGoGoUoAoCoGoAoG |
| 20 | pentyl | GoGoAoCoCoGoGoAoAoGoGoUoAoCoGoAoG |
| 21 | RNA | GoGoAoCoCoGoGoAoAoGoGoToAoCoGoAoG |
| | 18-mers | |
| 22 | 2'-deoxy | TsGsGsGsAsGsCsCsAsTsAsGsCsGsAsGsGsC |
| 23 | methy | TsGsGsGsAsGsCsCsAsTsAsGsCsGsAsGsGsC |
| 24 | propyl | TsGsGsGsAsGsCsCsAsTsAsGsCsGsAsGsGsC |
| 25 | pentyl | TsGsGsGsAsGsCsCsAsTsAsGsCsGsAsGsGsC |
| 26 | RNA | TsGsGsGsAsGsCsCsAsTsAsGsCsGsAsGsGsC |

[1]$T_m$'s are in °C. and were measured vs. RNA complements in 100 mM Na$^+$, 10 mM phosphate, 0.1 mM EDTA, pH 7.0 at 4 mM strand concentration. (P=O, phosphodiester, P=S, phosphorothioate)
[2]ND = not determined.
[3]$T_m$'s were measured without a complementary strand in 100 mM Na$^+$, 10 mM phosphate, 0.1 mM EDTA, pH 7.0 at 4 mM strand concentration.
underlined = 2' modified residue; o = phosphodiester linkage; s = phosphorothioate linkage

EXAMPLE 42

RNase ONE Footprinting Assay with ras RNA

The ras 47-mer stem/loop RNA was incubated at a concentration of 3–30 pM with oligonucleotides that were complementary to the preferred hybridization sites on the target. These oligonucleotides were synthesized using commercially available (Glen Research) 2'-O-methyl amidites, at a concentration of 10 μM in 10 mM Tris buffer (pH 8) consisting of 50 mM NaCl and 5 mM MgCl$_2$. The hybridization was carried out for at least 16 hours at 37° C. RNase ONE (10 μg/μL, Promega) was added in 1:2000 to 1:100,000 dilutions, incubated at 25° C. for 5 minutes, and quenched by snap freezing. A "G" map, using RNase Tl, and base ladder, using 50 mM Na$_2$CO$_3$ buffer (pH 9), were prepared. The digestion products were resolved by sequencing PAGE in order to identify at least one oligonucleotide that exhibits an RNase ONE footprint at 10 μM. The K$_d$ for an oligonucleotide of interest was then determined by titrating that oligonucleotide, at concentrations ranging from 100 pM to 10 μM, with RNase ONE. The digestion products were separated by sequencing PAGE and the percent protection afforded by the oligonucleotide was plotted as a function of the oligonucleotide concentration. The concentration of oligonucleotide at which 50% protection is observed is the K$_d$ for that oligonucleotide of interest. Using this method, oligonucleotides with enhanced affinity and specificity for the target ras RNA were identified.

EXAMPLE 43 ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. The plasmids pT24-C3, containing the c-H-ras1 activated oncogene (codon 12, GGC→GTC), and pbc-N1, containing the c-H-ras proto-oncogene, were obtained from the American Type Culture Collection (Bethesda, Md.). The plasmid pT3/T7 luc, containing the 1.9 kb firefly luciferase gene, was obtained from Clontech Laboratories (Palo Alto, Calif.). The oligonucleotide PCR primers were used in standard PCR reactions using mutant and non-mutant H-ras genes as templates. These primers produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were used in standard PCR reactions using a commercially available plasmid (pT3/T7-Luc) (Clontech), containing the luciferase reporter gene, as a template. These primers yield a product of approximately 1.9 kb corresponding to the luciferase gene, flanked by unique HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter. These plasmid constructions contain sequences encoding amino acids 1–22 of activated (RA2) or normal (RA4) H-ras proteins fused in frame with sequences coding for firefly luciferase. Translation initiation of the ras-luciferase fusion mRNA is dependent upon the natural H-ras AUG codon. Both mutant and normal H-ras luciferase fusion constructions were confirmed by DNA sequence analysis using standard procedures.

EXAMPLE 44

Transfection of Cells with Plasmid DNA

Transfections were performed as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY, with the following modifications. HeLa cells were plated on 60 mm dishes at $5\times10^5$ cells/dish. A total of 10 μg or 12 μg of DNA was added to each dish, of which 1 μg was a vector expressing the rat glucocorticoid receptor under control of the constitutive Rous sarcoma virus (RSV) promoter and the remainder was ras-luciferase reporter plasmid (Example 43). Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pre-treated with oligonucleotides prior to activation of reporter gene expression by dexamethasone.

EXAMPLE 45

Oligonucleotide Treatment of Cells

Following plasmid transfection (Example 44), cells were washed with phosphate buffered saline prewarmed to 37° C. and Opti-MEM containing 5 μg/mL N-[1-(2,3-dioleyloxy) propyl]-N,N,N,-trimethylammonium chloride (DOTMA) was added to each plate (1.0 ml per well). oligonucleotides were added from 50 μM stocks to each plate and incubated for 4 hours at 37° C. Medium was removed and replaced with DMEM containing 10% fetal bovine serum and the appropriate oligonucleotide at the indicated concentrations and cells were incubated for an additional 2 hours at 37° C. before reporter gene expression was activated by treatment of cells with dexamethasone to a final concentration of 0.2 μM. Cells were harvested and assayed for luciferase activity fifteen hours following dexamethasone stimulation.

EXAMPLE 46

Luciferase Assays

Luciferase was extracted from cells by lysis with the detergent Triton X-100 as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. A Dynatech ML1000 luminometer was used to measure peak luminescence upon addition of luciferin (Sigma) to 625 μM. For each extract, luciferase assays were performed multiple times, using differing amounts of extract to ensure that the data were gathered in the linear range of the assay.

EXAMPLE 46

Melting Curves

Absorbance vs temperature curves were measured at 260 nm using a Gilford 260 spectrophotometer interfaced to an IBM PC computer and a Gilford Response II spectrophotometer. The buffer contained 100 mM Na$^+$, 10 mM phosphate and 0.1 mM EDTA, pH 7. Oligonucleotide concentration was 4 μM each strand determined from the absorbance at 85° C. and extinction coefficients calculated according to Puglisi and Tinoco, *Methods in Enzymol.* 1989, 180, 304–325. $T_m$ values, free energies of duplex formation and association constants were obtained from fits of data to a two state model with linear sloping baselines. Petersheim, M. and Turner, D. H., *Biochemistry* 1983, 22, 256–263. Reported parameters are averages of at least three experiments. For some oligonucleotides, free energies of duplex formation were also obtained from plots of $T_m^{-1}$ $\log_{10}$ (concentration). Borer, P. N., Dengler, B., Tinoco, I., Jr., and Uhlenbeck, O. C., *J. Mol. Biol.*, 1974, 86, 843–853.

EXAMPLE 47

Activity of Oligonucleotides Having 2'-O-Substituted Pyrimidine Nucleosides

Using the procedures of Examples 43–46, oligomeric compounds were tested for hybridization affinity to complementary RNA and for activity against the Ha-ras oncogene in cells. Uniformly 2'-O-modified oligomers and chimeric oligomers having both 2'-O-modified and 2'-deoxy regions were examined. Uniformly 2'-O-modified oligomers including 2'-O-methyl, 2'-O-propyl, and 2'-O-pentyl showed greater affinity to RNA than unmodified 2'-deoxy oligonucleotide. Chimeric oligomers having both 2'-O-modified and 2'-deoxy regions showed greater affinity to RNA than unmodified 2'-deoxy oligonucleotide and also showed significant inhibition of Ha-ras gene expression compared with unmodified uniform deoxy phosphorothioate (see Monia, B. P., et.al., *J. Biol. Chem.*, 1993, 268, 14514–14522).

Each of the published documents mentioned in this specification are herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A process for the synthesis of a 2'-O-substituted pyrimidine nucleoside of formula:

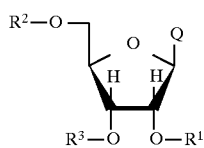

wherein:

Q is a pyrimidine base or a 2-S pyrimidine base;

$R^1$ is substituted or unsubstituted $C_1$–$C_{30}$ alkyl, $C_1$–$C_{30}$ alkenyl, $C_1$–$C_{30}$ alkynyl, $C_6$–$C_{14}$ aryl, or $C_7$–$C_{30}$ aralkyl, wherein said substitution is halo, amino, hydroxyl, thiol, ether or thioether; and $R^2$ and $R^3$ are independently hydrogen or a hydroxyl protecting group;

comprising the steps of:

providing a 2-2'-anhydropyrimidine nucleoside;

selecting an alcohol of the formula $R^1$-OH; and treating said 2-2'-anhydropyrimidine nucleoside and said alcohol with a Lewis acid under conditions of time, temperature and pressure effective to yield said 2'-O-substituted pyrimidine nucleoside.

2. The process of claim 1 wherein said 2-2'-anhydropyrimidine nucleoside and said alcohol are treated in a pressure sealed vessel.

3. The process of claim 1 wherein $R^1$ is $C_1$–$C_{10}$ alkyl.

4. The process of claim 1 wherein $R^1$ is $C_6$–$C_{14}$ aryl.

5. The process of claim 1 wherein said treating comprises heating at from about 120° C. to about 200° C.

6. The process of claim 1 wherein said pyrimidine nucleoside is uridine or 5-methyluridine.

7. A process for the synthesis of a 2'-O-substituted cytidine nucleoside of formula:

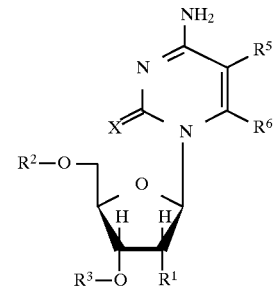

wherein:

X is O or S;

$R^1$ is substituted or unsubstituted $C_1$–$C_{30}$ alkyl, $C_1$–$C_{30}$ alkenyl, $C_1$–$C_{30}$ alkynyl, $C_6$–$C_{14}$ aryl, or $C_7$–$C_{30}$ aralkyl, wherein said substitution is halo, amino, hydroxyl, thiol, ether or thioether;

$R^2$ and $R^3$ are independently hydrogen or a hydroxyl protecting group;

$R^5$ and $R^6$ are independently H, $C_1$–$C_{30}$ hydrocarbyl or substituted $C_1$–$C_{30}$ hydrocarbyl;

comprising the steps of:

providing a 2-2'-anhydrouridine nucleoside of formula:

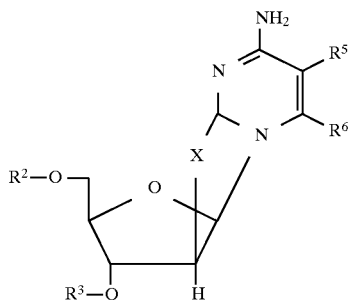

selecting an alcohol of formula $R^1$-OH;

treating said 2-2'-anhydrouridine nucleoside and said alcohol with a Lewis acid under conditions of time, temperature and pressure effective to form a 2'-O-substituted uridine nucleoside; and aminating said 2'-O-substituted uridine nucleoside to said 2'-O-substituted cytidine nucleoside.

8. The process of claim 12 wherein said 2-2'-anhydrouridine nucleoside and said alcohol are treated in a pressure sealed vessel.

9. The process of claim 7 wherein $R^1$ is $C_1$–$C_{10}$ alkyl.

10. The process of claim 7 wherein $R^1$ is $C_6$–$C_{14}$ aryl.

11. The process of claim 7 wherein said treating comprises heating from about 120° C. to about 200° C.

12. The process of claim 7 wherein said 2'-O-substituted cytidine nucleoside is 2'-O-methyl-5-methylcytidine.

* * * * *

UNITED STATES PATENT AND TRADEMARK OFFICE
CERTIFICATE OF CORRECTION

PATENT NO. : 5,861,493
DATED : 1/19/99
INVENTOR(S) : Cook et al.

It is certified that error appears in the above-identified patent and that said Letters Patent is hereby corrected as shown below:

Column 23, line 23, delete "(µgSB," and insert therefor --(USB,--;
Column 24, line 26, delete "≥" and insert therefor -->--;
Under "FOREIGN PATENT DOCUMENTS" "1-85456" should read
--8985456    4/1989    Japan--

Signed and Sealed this

Twelfth Day of September, 2000

Attest:

Q. TODD DICKINSON

Attesting Officer

Director of Patents and Trademarks